US012168075B2

United States Patent
Lee et al.

(10) Patent No.: US 12,168,075 B2
(45) Date of Patent: *Dec. 17, 2024

(54) SYSTEMS COMPRISING A COMPOSITE BACKING AND METHODS FOR LONG TERM TRANSDERMAL ADMINISTRATION

(71) Applicant: Corium, LLC, Boston, MA (US)

(72) Inventors: Eun Soo Lee, Redwood City, CA (US); Amit K. Jain, Milpitas, CA (US); Parminder Singh, Union City, CA (US)

(73) Assignee: Corium, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/312,129

(22) Filed: May 4, 2023

(65) Prior Publication Data

US 2024/0108587 A1 Apr. 4, 2024

Related U.S. Application Data

(63) Continuation of application No. 17/200,481, filed on Mar. 12, 2021, now Pat. No. 11,679,086, which is a
(Continued)

(51) Int. Cl.
*A61K 9/70* (2006.01)
*A61K 9/00* (2006.01)
(Continued)

(52) U.S. Cl.
CPC .......... *A61K 9/7084* (2013.01); *A61K 9/0014* (2013.01); *A61K 9/7053* (2013.01);
(Continued)

(58) Field of Classification Search
CPC ...... A61K 9/7084; A61K 9/70; A61K 9/7007; A61K 9/7015; A61K 47/34; A61K 41/00;
(Continued)

(56) References Cited

U.S. PATENT DOCUMENTS 1,683,347 A 9/1928 Gray et al.
1,698,049 A 1/1929 Clarke et al.
(Continued)

FOREIGN PATENT DOCUMENTS

CA 2332012 A1 11/1999
CN 1174031 A 2/1998
(Continued)

OTHER PUBLICATIONS (2012) "Formulation and Evaluation of Matrix Type Transdermal Patched of Benazepril Hydrochloride", Dissertation submitted by R. Revathi, Reg. No. 26108606, to the Controller of Examination, Department of Pharmaceutics College of Pharmacy, Madurai Medical College, Madurai, The Tamilnadu, 202 pages.
(Continued)

*Primary Examiner* — Ophelia A Hawthorne
(74) *Attorney, Agent, or Firm* — Mintz, Levin, Cohn, Ferris, Glovsky and Popeo, P.C.

(57) ABSTRACT

Devices, systems, compositions and methods for long term or prolonged transdermal administration of an active agent are provided.

11 Claims, 3 Drawing Sheets

Related U.S. Application Data continuation of application No. 15/396,236, filed on Dec. 30, 2016, now Pat. No. 10,966,936.

(60) Provisional application No. 62/367,055, filed on Jul. 26, 2016, provisional application No. 62/273,288, filed on Dec. 30, 2015.

(51) Int. Cl.
*A61K 41/00* (2020.01)
*A61K 47/34* (2017.01)
*A61M 35/00* (2006.01)

(52) U.S. Cl.
CPC .......... *A61K 9/7061* (2013.01); *A61K 9/7069* (2013.01); *A61K 41/00* (2013.01); *A61K 47/34* (2013.01); *A61M 35/00* (2013.01); *A61K 9/703* (2013.01)

(58) Field of Classification Search
CPC ........ A61L 15/58; A61L 15/42; A61L 15/225; A61L 2420/08; A61L 15/00; A61L 26/00; A61F 13/0259; A61F 13/0253; A61F 13/0243; A61F 2013/53925; A61F 13/00; A61F 5/443; A61F 13/0246
See application file for complete search history.

(56) References Cited

U.S. PATENT DOCUMENTS

| | | |
|---|---|---|
| 1,880,560 A | 10/1932 | Webber et al. |
| 1,880,808 A | 10/1932 | Clarke et al. |
| 1,939,729 A | 12/1933 | Stark |
| 1,943,119 A | 1/1934 | James |
| 1,984,147 A | 12/1934 | Malm |
| 2,129,052 A | 9/1938 | Fordyce |
| 3,391,142 A | 7/1968 | Jack et al. |
| 3,546,141 A | 12/1970 | Washburn et al. |
| 3,549,016 A | 12/1970 | Rigopulos |
| 3,617,201 A | 11/1971 | Berni et al. |
| 4,004,654 A | 1/1977 | Hamy |
| 4,122,193 A | 10/1978 | Scherm et al. |
| 4,273,774 A | 6/1981 | Scherm |
| 4,752,478 A | 6/1988 | Bondi et al. |
| 4,756,710 A | 7/1988 | Bondi et al. |
| 4,781,924 A | 11/1988 | Lee et al. |
| 4,787,888 A | 11/1988 | Fox |
| 4,797,284 A | 1/1989 | Loper et al. |
| 4,821,845 A | 4/1989 | Deviaris |
| 4,837,027 A | 6/1989 | Lee et al. |
| 4,849,224 A | 7/1989 | Chang et al. |
| 4,880,633 A | 11/1989 | Loper et al. |
| 4,886,812 A | 12/1989 | Griss et al. |
| 4,895,841 A | 1/1990 | Sugimoto et al. |
| 5,026,556 A | 6/1991 | Drust et al. |
| 5,061,703 A | 10/1991 | Bormann et al. |
| 5,071,656 A | 12/1991 | Lee et al. |
| 5,123,900 A | 6/1992 | Wick |
| 5,132,115 A | 7/1992 | Wolter et al. |
| 5,202,128 A | 4/1993 | Morella et al. |
| 5,246,705 A | 9/1993 | Venkatraman et al. |
| 5,252,588 A | 10/1993 | Azuma et al. |
| 5,284,660 A | 2/1994 | Lee et al. |
| 5,296,512 A | 3/1994 | Beier et al. |
| 5,362,497 A | 11/1994 | Yamada et al. |
| 5,424,077 A | 6/1995 | Lajoie |
| 5,538,736 A | 7/1996 | Hoffmann et al. |
| 5,567,489 A | 10/1996 | Allen et al. |
| 5,601,156 A | 2/1997 | Mccarthy et al. |
| 5,612,411 A | 3/1997 | Gross |
| 5,614,211 A | 3/1997 | Gale et al. |
| 5,614,560 A | 3/1997 | Lipton |
| 5,635,203 A | 6/1997 | Gale et al. |
| 5,651,426 A | 7/1997 | Bittar et al. |
| 5,660,178 A | 8/1997 | Kantner et al. |
| 5,662,925 A | 9/1997 | Ebert et al. |
| 5,686,489 A | 11/1997 | Yu et al. |
| 5,730,900 A | 3/1998 | Kawata |
| 5,730,999 A | 3/1998 | Lehmann et al. |
| 5,752,585 A | 5/1998 | Bittar et al. |
| 5,758,748 A | 6/1998 | Barker et al. |
| 5,785,153 A | 7/1998 | Powell et al. |
| 5,843,468 A | 12/1998 | Burkoth et al. |
| 5,861,586 A | 1/1999 | Mccarthy et al. |
| 5,866,585 A | 2/1999 | Fogel |
| 5,924,524 A | 7/1999 | Barker et al. |
| 5,958,919 A | 9/1999 | Olney et al. |
| 5,985,864 A | 11/1999 | Imai |
| 6,004,578 A | 12/1999 | Lee et al. |
| 6,174,545 B1 | 1/2001 | Enscore et al. |
| 6,225,348 B1 | 5/2001 | Paulsen |
| 6,383,471 B1 | 5/2002 | Chen et al. |
| 6,512,010 B1 | 1/2003 | Gale et al. |
| 6,521,639 B1 | 2/2003 | Murahashi et al. |
| 6,576,712 B2 | 6/2003 | Feldstein et al. |
| 6,746,689 B2 | 6/2004 | Fischer et al. |
| 6,803,420 B2 | 10/2004 | Cleary et al. |
| 6,923,988 B2 | 8/2005 | Patel et al. |
| 6,929,801 B2 | 8/2005 | Klose et al. |
| 7,097,853 B1 | 8/2006 | Garbe et al. |
| 7,138,458 B2 | 11/2006 | Cleary et al. |
| 7,176,185 B2 | 2/2007 | Hilfinger et al. |
| 7,217,853 B2 | 5/2007 | Kulichikhin et al. |
| 7,250,394 B2 | 7/2007 | Nedergaard |
| 7,320,802 B2 | 1/2008 | Ryde et al. |
| 7,335,379 B2 | 2/2008 | Carrara et al. |
| 7,456,331 B2 | 11/2008 | Kulichikhin et al. |
| 7,462,743 B2 | 12/2008 | Merli et al. |
| 7,670,838 B2 | 3/2010 | Deisseroth et al. |
| 7,682,628 B2 | 3/2010 | Singh |
| 7,744,918 B2 | 6/2010 | Yamaguchi et al. |
| 7,824,707 B2 | 11/2010 | Hille et al. |
| 7,858,114 B2 | 12/2010 | Ito |
| 7,888,422 B2 | 2/2011 | Jackson et al. |
| 8,058,291 B2 | 11/2011 | Went et al. |
| 8,168,209 B2 | 5/2012 | Went et al. |
| 8,206,738 B2 | 6/2012 | Singh et al. |
| 8,246,978 B2 | 8/2012 | Kydonieus et al. |
| 8,252,321 B2 | 8/2012 | Dipierro et al. |
| 8,273,405 B2 | 9/2012 | Feldstein et al. |
| 8,283,379 B2 | 10/2012 | Went et al. |
| 8,362,085 B2 | 1/2013 | Went et al. |
| 8,481,059 B2 | 7/2013 | Cleary et al. |
| 8,481,071 B2 | 7/2013 | Singh et al. |
| 8,486,443 B2 | 7/2013 | Schuhmacher et al. |
| 8,512,742 B2 | 8/2013 | Amano et al. |
| 8,541,021 B2 | 9/2013 | Singh et al. |
| 8,614,274 B2 | 12/2013 | Jackson et al. |
| 8,617,647 B2 | 12/2013 | Feldstein et al. |
| 8,658,201 B2 | 2/2014 | Singh et al. |
| 8,673,338 B2 | 3/2014 | Bleier |
| 8,728,445 B2 | 5/2014 | Cleary et al. |
| 8,741,331 B2 | 6/2014 | Singh et al. |
| 8,753,669 B2 | 6/2014 | Cleary et al. |
| 8,784,879 B2 | 7/2014 | Singh et al. |
| 8,815,281 B2 | 8/2014 | Kanios et al. |
| 8,821,901 B2 | 9/2014 | Feldstein et al. |
| 8,840,918 B2 | 9/2014 | Singh et al. |
| 8,840,922 B2 | 9/2014 | Kawakami et al. |
| 8,840,935 B2 | 9/2014 | Haber et al. |
| 8,874,879 B2 | 10/2014 | Ge et al. |
| 9,012,511 B2 | 4/2015 | Neville et al. |
| 9,078,833 B2 | 7/2015 | Audett |
| 9,095,653 B2 | 8/2015 | Willmann et al. |
| 9,248,104 B2 | 2/2016 | Valia et al. |
| 9,408,802 B1 | 8/2016 | Hartwig |
| 9,598,265 B1 | 3/2017 | Jacobs |
| 9,622,986 B2 | 4/2017 | Im et al. |
| 9,993,466 B2 | 6/2018 | Lee et al. |
| 10,106,372 B2 | 10/2018 | Jetter et al. |
| 10,300,025 B2 | 5/2019 | Lee et al. |
| 10,307,379 B2 | 6/2019 | Lee et al. |
| 10,835,499 B2 | 11/2020 | Lee et al. |
| 10,945,968 B2 | 3/2021 | Lee et al. |

(56) References Cited

U.S. PATENT DOCUMENTS

| | | | |
|---|---|---|---|
| 10,966,936 B2 | 4/2021 | Lee et al. | |
| 11,103,463 B2 | 8/2021 | Lee et al. | |
| 11,173,132 B2 | 11/2021 | Lee et al. | |
| 11,541,018 B2 | 1/2023 | Lee et al. | |
| 11,648,214 B2 | 5/2023 | Lee et al. | |
| 11,679,086 B2 * | 6/2023 | Lee | A61K 41/00 604/290 |
| 2001/0031787 A1 | 10/2001 | Hsu et al. | |
| 2002/0192243 A1 | 12/2002 | Hsu et al. | |
| 2003/0099694 A1 | 5/2003 | Cevc et al. | |
| 2003/0152528 A1 | 8/2003 | Singh et al. | |
| 2003/0170308 A1 | 9/2003 | Cleary et al. | |
| 2003/0217893 A1 | 11/2003 | Dünser et al. | |
| 2003/0225356 A1 | 12/2003 | Kulichikhin et al. | |
| 2004/0018241 A1 | 1/2004 | Houze et al. | |
| 2004/0022835 A1 | 2/2004 | Pai et al. | |
| 2004/0024028 A1 | 2/2004 | Burton | |
| 2004/0028724 A1 | 2/2004 | Terahara et al. | |
| 2004/0033254 A1 | 2/2004 | Song et al. | |
| 2004/0087658 A1 | 5/2004 | Moebius | |
| 2004/0105834 A1 | 6/2004 | Singh et al. | |
| 2004/0180080 A1 | 9/2004 | Furusawa et al. | |
| 2004/0258723 A1 | 12/2004 | Singh et al. | |
| 2005/0041376 A1 | 2/2005 | Peuscher et al. | |
| 2005/0049356 A1 | 3/2005 | Zanzig | |
| 2005/0113458 A1 | 5/2005 | Gupta et al. | |
| 2005/0189181 A1 | 9/2005 | Meyle et al. | |
| 2005/0208110 A1 | 9/2005 | Singh et al. | |
| 2005/0244485 A1 | 11/2005 | Hsu et al. | |
| 2006/0016640 A1 | 1/2006 | Duenser et al. | |
| 2006/0034905 A1 | 2/2006 | Singh et al. | |
| 2006/0035888 A1 | 2/2006 | Jonas et al. | |
| 2006/0163008 A1 | 7/2006 | Godwin | |
| 2006/0171906 A1 | 8/2006 | Singh et al. | |
| 2006/0188558 A1 | 8/2006 | Jackson et al. | |
| 2006/0205822 A1 | 9/2006 | Jonas et al. | |
| 2007/0184097 A1 | 8/2007 | Kurita et al. | |
| 2007/0259028 A1 | 11/2007 | Ito | |
| 2007/0259029 A1 | 11/2007 | Mcentire et al. | |
| 2008/0004329 A1 | 1/2008 | Jamieson et al. | |
| 2008/0025932 A1 | 1/2008 | Bissett et al. | |
| 2008/0038328 A1 | 2/2008 | Higo et al. | |
| 2008/0044461 A1 | 2/2008 | Valia et al. | |
| 2008/0107719 A1 | 5/2008 | Likitlersuang et al. | |
| 2008/0131490 A1 | 6/2008 | Hanatani et al. | |
| 2008/0131491 A1 | 6/2008 | Hanatani et al. | |
| 2008/0138388 A1 | 6/2008 | Aida et al. | |
| 2008/0161492 A1 | 7/2008 | Cleary et al. | |
| 2008/0226698 A1 | 9/2008 | Tang et al. | |
| 2009/0029926 A1 | 1/2009 | Lintner | |
| 2009/0060986 A1 | 3/2009 | Yum et al. | |
| 2009/0062754 A1 | 3/2009 | Tang | |
| 2009/0081259 A1 | 3/2009 | Jonas et al. | |
| 2009/0124659 A1 | 5/2009 | Moebius | |
| 2009/0156639 A1 | 6/2009 | Trippodi-Murphy et al. | |
| 2009/0175929 A1 | 7/2009 | Terahara et al. | |
| 2009/0258060 A1 | 10/2009 | Cleary et al. | |
| 2009/0291127 A1 | 11/2009 | Wen et al. | |
| 2009/0311199 A1 | 12/2009 | Hillman | |
| 2010/0031787 A1 | 2/2010 | Hu | |
| 2010/0121290 A1 | 5/2010 | Rasmussen et al. | |
| 2010/0178037 A1 | 7/2010 | Chen et al. | |
| 2010/0178307 A1 | 7/2010 | Wen et al. | |
| 2010/0227852 A1 | 9/2010 | Moebius | |
| 2010/0239644 A1 | 9/2010 | Feldstein et al. | |
| 2010/0291186 A1 | 11/2010 | Singh et al. | |
| 2011/0056863 A1 | 3/2011 | Sekiya et al. | |
| 2011/0059141 A1 | 3/2011 | Ito | |
| 2011/0059169 A1 | 3/2011 | Went et al. | |
| 2011/0066120 A1 | 3/2011 | Lee | |
| 2011/0111013 A1 | 5/2011 | Salman et al. | |
| 2011/0244023 A1 | 10/2011 | Cottrell et al. | |
| 2011/0313372 A1 | 12/2011 | Eifler et al. | |
| 2012/0027695 A1 | 2/2012 | Feldstein et al. | |
| 2012/0121729 A1 | 5/2012 | Paterson et al. | |
| 2012/0207816 A1 | 8/2012 | Kawakami et al. | |
| 2012/0237579 A1 | 9/2012 | Singh et al. | |
| 2012/0245537 A1 | 9/2012 | Horstmann et al. | |
| 2012/0321569 A1 | 12/2012 | Feldstein et al. | |
| 2012/0321690 A1 | 12/2012 | Toshimitsu et al. | |
| 2012/0323190 A1 | 12/2012 | Ito | |
| 2013/0053358 A1 | 2/2013 | Aida et al. | |
| 2013/0064868 A1 | 3/2013 | Okazaki et al. | |
| 2013/0095168 A1 | 4/2013 | Choi et al. | |
| 2013/0144226 A1 | 6/2013 | Takada | |
| 2013/0211353 A1 | 8/2013 | Toshimitsu et al. | |
| 2013/0261526 A1 | 10/2013 | Cleary et al. | |
| 2013/0273127 A1 | 10/2013 | Singh et al. | |
| 2013/0331803 A1 | 12/2013 | Fleschhut et al. | |
| 2014/0044650 A1 | 2/2014 | Singh et al. | |
| 2014/0052081 A1 | 2/2014 | Yang et al. | |
| 2014/0114049 A1 | 4/2014 | Jiao et al. | |
| 2014/0147489 A1 | 5/2014 | Singh et al. | |
| 2014/0148456 A1 | 5/2014 | Likitlersuang et al. | |
| 2014/0256690 A1 | 9/2014 | Rubin et al. | |
| 2014/0271781 A1 | 9/2014 | Singh et al. | |
| 2014/0276479 A1 | 9/2014 | Nguyen et al. | |
| 2014/0303574 A1 | 10/2014 | Knutson | |
| 2014/0322284 A1 | 10/2014 | Singh et al. | |
| 2014/0370076 A1 | 12/2014 | Choi et al. | |
| 2015/0080437 A1 | 3/2015 | Lee et al. | |
| 2015/0098980 A1 | 4/2015 | Pongpeerapat et al. | |
| 2016/0051486 A1 | 2/2016 | Choi et al. | |
| 2016/0075533 A1 | 3/2016 | Scomparin | |
| 2016/0199317 A1 | 7/2016 | Janisch et al. | |
| 2016/0256552 A1 | 9/2016 | Yamasaki | |
| 2016/0304316 A1 | 10/2016 | Witczak et al. | |
| 2016/0304317 A1 | 10/2016 | Witczak et al. | |
| 2017/0001829 A1 | 1/2017 | Jetter et al. | |
| 2017/0008729 A1 | 1/2017 | Ginsberg et al. | |
| 2017/0015524 A1 | 1/2017 | Fargo | |
| 2017/0057780 A1 | 3/2017 | Nguyen et al. | |
| 2017/0057784 A1 | 3/2017 | Witczak et al. | |
| 2017/0057786 A1 | 3/2017 | Witczak et al. | |
| 2017/0057790 A1 | 3/2017 | Roberts et al. | |
| 2017/0057792 A1 | 3/2017 | Dwari et al. | |
| 2017/0066623 A1 | 3/2017 | Kuczek et al. | |
| 2017/0073183 A1 | 3/2017 | Ginsberg et al. | |
| 2017/0088395 A1 | 3/2017 | Roberts et al. | |
| 2017/0088396 A1 | 3/2017 | Fargo | |
| 2017/0088398 A1 | 3/2017 | Kuczek et al. | |
| 2017/0158461 A1 | 6/2017 | Roberts et al. | |
| 2017/0189348 A1 | 7/2017 | Lee et al. | |
| 2017/0189534 A1 | 7/2017 | Lee et al. | |
| 2017/0190544 A1 | 7/2017 | Witczak et al. | |
| 2017/0202830 A1 | 7/2017 | Stinchcomb et al. | |
| 2017/0233218 A1 | 8/2017 | Zheng et al. | |
| 2017/0240385 A1 | 8/2017 | Fargo | |
| 2017/0360908 A1 | 12/2017 | Shishido et al. | |
| 2018/0028461 A1 | 2/2018 | Singh et al. | |
| 2018/0028462 A1 | 2/2018 | Lee et al. | |
| 2018/0028463 A1 | 2/2018 | Lee et al. | |
| 2018/0028466 A1 | 2/2018 | Lee et al. | |
| 2018/0028467 A1 | 2/2018 | Singh et al. | |
| 2018/0028512 A1 | 2/2018 | Lee et al. | |
| 2018/0028663 A1 | 2/2018 | Lee et al. | |
| 2018/0185298 A1 | 7/2018 | Jain et al. | |
| 2018/0235901 A1 | 8/2018 | Lee et al. | |
| 2018/0284666 A1 | 10/2018 | Fujii et al. | |
| 2019/0029971 A1 | 1/2019 | Lee et al. | |
| 2019/0231709 A1 | 8/2019 | Lee et al. | |
| 2019/0247320 A1 | 8/2019 | Lee et al. | |
| 2021/0015761 A1 | 1/2021 | Lee et al. | |
| 2022/0016045 A1 | 1/2022 | Lee et al. | |
| 2023/0072739 A1 | 3/2023 | Lee et al. | |
| 2023/0086303 A1 | 3/2023 | Singh et al. | |
| 2023/0145274 A1 | 5/2023 | Lee et al. | |
| 2024/0041791 A1 | 2/2024 | Jain | |
| 2024/0082172 A1 | 3/2024 | Jain | |
| 2024/0091168 A1 | 3/2024 | Lee | |
| 2024/0108587 A1 | 4/2024 | Lee | |
| 2024/0156747 A1 | 5/2024 | Lee | |

(56) References Cited

U.S. PATENT DOCUMENTS

FOREIGN PATENT DOCUMENTS

| | | |
|---|---|---|
| CN | 1176932 A | 3/1998 |
| CN | 1205630 A | 1/1999 |
| CN | 1462718 A | 12/2003 |
| CN | 1668521 A | 9/2005 |
| CN | 101518599 A | 9/2009 |
| CN | 102048678 A | 5/2011 |
| CN | 1895242 B | 8/2011 |
| CN | 105693556 A | 6/2016 |
| EP | 0296560 A2 | 12/1988 |
| EP | 0377518 A2 | 7/1990 |
| EP | 0481443 A1 | 4/1992 |
| EP | 0540623 B1 | 9/1994 |
| EP | 1423100 A1 | 6/2004 |
| EP | 1526103 A1 | 4/2005 |
| EP | 1616832 A2 | 1/2006 |
| EP | 1619157 A1 | 1/2006 |
| EP | 1682109 B1 | 10/2008 |
| EP | 2016941 A1 | 1/2009 |
| EP | 2090310 A1 | 8/2009 |
| EP | 2098233 A1 | 9/2009 |
| EP | 2098235 A1 | 9/2009 |
| EP | 2196197 A1 | 6/2010 |
| EP | 2260839 A2 | 12/2010 |
| EP | 2514415 A1 | 10/2012 |
| EP | 2638906 A1 | 9/2013 |
| EP | 2818161 A1 | 12/2014 |
| IE | 61005 B1 | 9/1994 |
| JP | S61275213 A | 12/1986 |
| JP | H06199659 A | 7/1994 |
| JP | H06321445 A | 11/1994 |
| JP | H07112875 A | 5/1995 |
| JP | H10310337 A | 11/1998 |
| JP | 2008259629 A | 10/2008 |
| JP | 2009013171 A | 1/2009 |
| JP | 2009203213 A | 9/2009 |
| JP | 2013075856 A | 4/2013 |
| JP | 2015151370 A | 8/2015 |
| KR | 20090101667 A | 9/2009 |
| WO | 9518603 A1 | 7/1995 |
| WO | 9610047 A1 | 4/1996 |
| WO | 9619205 A1 | 6/1996 |
| WO | 9640087 A2 | 12/1996 |
| WO | 02087645 A1 | 11/2002 |
| WO | 03020248 A1 | 3/2003 |
| WO | 03055471 A1 | 7/2003 |
| WO | 2005079779 A1 | 9/2005 |
| WO | 2006091442 A2 | 8/2006 |
| WO | 2007132476 A2 | 11/2007 |
| WO | 2008021113 A2 | 2/2008 |
| WO | WO2008024408 | 2/2008 |
| WO | 2009026135 A2 | 2/2009 |
| WO | 2009032184 A1 | 3/2009 |
| WO | 2010051349 A1 | 5/2010 |
| WO | 2011070361 A1 | 6/2011 |
| WO | 2011081628 A1 | 7/2011 |
| WO | 2012084969 A1 | 6/2012 |
| WO | 2012089256 A1 | 7/2012 |
| WO | 2012097197 A1 | 7/2012 |
| WO | 2013078608 A1 | 6/2013 |
| WO | 2013112806 A2 | 8/2013 |
| WO | 2014174564 A1 | 10/2014 |
| WO | 2015053878 A1 | 4/2015 |
| WO | 2015200472 A1 | 12/2015 |
| WO | 2016046675 A1 | 3/2016 |
| WO | 2016099198 A1 | 6/2016 |
| WO | 2016209982 A1 | 12/2016 |
| WO | 2017018321 A1 | 2/2017 |
| WO | 2017117554 A1 | 7/2017 |
| WO | 2017223402 A1 | 12/2017 |
| WO | 2018022814 A1 | 2/2018 |
| WO | 2018022815 A2 | 2/2018 |
| WO | 2018022816 A1 | 2/2018 |
| WO | 2018022817 A1 | 2/2018 |
| WO | 2018022818 A1 | 2/2018 |
| WO | WO2019023499 | 1/2019 |
| WO | WO2023278978 | 1/2023 |
| WO | WO2024145319 | 7/2024 |
| WO | WO2024145323 | 7/2024 |

OTHER PUBLICATIONS (2019) "Fumed Metal Oxides", Cabot Corporation, www.cabotcorp.com/solutions/products-plus/fumed-metl-oxides, 5 pages.

International Search Report and Written Opinion for International Application No. PCT/EP2015/000167, mailed on May 13, 2015, 16 pages.

International Search Report and Written Opinion for International Application No. PCT/US2016/038792, mailed on Sep. 27, 2016, 15 pages.

International Search Report and Written Opinion for International Application No. PCT/US2017/038934, mailed on Oct. 10, 2017, 10 pages.

International Search Report and Written Opinion for International Application No. PCT/US2017/044047, mailed on Nov. 3, 2017, 14 pages.

International Search Report and Written Opinion for International Application No. PCT/US2017/044049, mailed on Nov. 7, 2017, 14 pages.

International Search Report and Written Opinion for International Application No. PCT/US2017/044050, mailed on Nov. 6, 2017, 12 pages.

International Search Report and Written Opinion for International Application No. PCT/US2017/044051, mailed on Nov. 2, 2017, 11 pages.

International Search Report and Written Opinion for International Application No. PCT/US2018/043961, mailed on Nov. 23, 2018, 12 pages.

International Search Report and Written Opinion for International Application No. PCT/US2018/066848, mailed on Apr. 15, 2019, 17 pages.

International Search Report and Written Opinion from International Patent Application No. PCT/US2022/073190, mailed on Mar. 9, 2023, 13 pages.

International Search Report and Written Opinion issued in International Application No. PCT/US2014/056118, mailed on Feb. 11, 2015, 10 pages.

International Search Report and Written Opinion issued in International Application No. PCT/US2016/069558, mailed on Apr. 26, 2017, 11 pages.

International Search Report and Written Opinion issued in International Application No. PCT/US2018/065551, mailed on Mar. 14, 2019, 8 pages.

International Search Report from International Patent Application No. PCT/US2017/044048, mailed Nov. 3, 2017, 17 pages.

(2018) "Lidocaine", RN: 137-58-6, U.S. National Library of Medicine, 8600 Rockville Pike, bathesda, MD 20894, National Institute of Health, 6 pages.

(2018) "Ropinirole", ChemIDp/us, RN: 91374-21-9, U.S. National Library of Medicine, 8600 Rockville Pike, Bathesda, MD 20894, National Institute of Health, 3 pages.

Ashall (Nov. 30, 2013) "Tobacco Facts #4: Smokers are Freebasing Nicotine!—The Great Tobacco Plague", https://biochemdr1.wordpress.com/2013/11/30/tobacco-fact-4-somkers-are-freebasing-nicotine/, 5 pages.

Brantseva et al. (Mar. 2016) "Rheological and Adhesive Properties of PIB-Based Pressure-Sensitive Adhesives with Montmorillonite-Type Nanofillers", European Polymer Journal, 76:228-244.

Chladek et al. (2008) "Steady-State Bioequivalence Studies of Two Memantine Tablet and Oral Solution Formulations in Healthy Volunteers", Journal of Applied Biomedicine, 6:39-45.

Choi et al. (2012) "Effect of Fatty Acids on the Transdermal Delivery of Donepezil: in Vitro and in Vivo Evaluation", International Journal of Pharmaceutics, 422(1-2):83-90.

Forchetti M.C. (Aug. 15, 2005) "Treating Patients With Moderate to Severe Alzheimer's Disease: Implications of Recent Pharmacologic

(56) References Cited

OTHER PUBLICATIONS

Studies", Primary Care Companion to the Journal of Clinical Psychiatry (PMID: 16163398), 7(4):155-161.

Fornasari et al. (2017) "Synthesis and Antioxidant Properties of Novel Memantine Derivatives", Central Nervous System Agents in Medicinal Chemistry, 17(2):123-128.

Jain et al. (2005) "High Throughput Screening of Transdermal Penetration Enhancers: Opportunities, Methods, and Applications", Percutaneous Penetration Enhancers, CRC Press, Chapter 22:319-333.

Lee et al. (2007) "pH-Controlled, Polymer-Mediated Assembly of Polymer Micelle Nanoparticles", Langmuir, 23(2):488-495.

Mittapelly et al. (2018) "In Depth Analysis of Pressure-Sensitive Adhesive Patch-Assisted Delivery of Memantine and Donepezil Using Physiologically Based Pharmacokinetic Modeling and in Vitro/in Vivo Correlations", Molecular Pharmaceutics, 15(7):2646-2655.

Ogiso et al. (1989) "Membrane-Controlled Transdermal Therapeutic System Containing Clonazepam and Anticonvulsant Activity After Its Application", Chemical and Pharmaceutical Bulletin, 37(2):446-449.

Pastore et al. (2015) "Transdermai Patches: History, Development and Pharmacology", British Journal of Pharmacology, 172(9):2179-2209.

Ravi et al. (2015) "The Treatment of Alzheimers Disease by Using Donopezil Loaded Transdermal Patch", Journal of Chemical and Pharmaceutical Research, 7(3):806-813.

Del Rio-Sancho et al. (Sep. 2012) "Transdermal Absorption of Memantin—Effect of Chemical Enhancers, Iontophoresis, and Role of Enhancer Lipophilicity", European Journal of Pharmaceutics and Biopharmaceutics, 82(1):164-170.

Del Rio-Sancho et al. (2017) "Transdermal Therapeutic Systems for Memantine Delivery. Comparison of Passive and Iontophoretic Transport", International Journal of Pharmaceutics, 517(1-2):104-111.

Saluja et al. (2013) "A Novel Electronic Skin Patch for Delivery and Pharmacokinetic Evaluation of Donepezil Following Transdermal Iontophoresis", International Journal of Pharmaceutics, 453(2):395-399.

Schulz et al. (2012) "Therapeutic and Toxic Blood Concentrations of Nearly 1,000 Drugs and Other Xenobiotics", Critical Care, 16(4):R136 (4 pages).

Shivalingam et al. (2014) "Formulation and Evaluation of Diclofenac Potassium Transdermal Patches for Enhanced Therapeutic Efficacy", Indian Journal of Research in Pharmacy and Biotechnology, 1152-1157.

Sozio et al. (Aug. 20, 2012) "Transdermal Donepezil on the Treatment of Alzheimer's Disease", Neuropsychiatric Disease and Treatment, 8:361-368.

Aida et al, "Adhesive patch useful in pharmaceuticals, for delivering drugs, provides single surface of support with adhesive iayer, where adhesive layer contains drug in solution stae and crystalline state", Database WPI, AN 2008-F37689 (2013).

Fang et al., "Donepezll percutaneous absorption enhancer and back lining layer which includes polyethylene, polyester and ethylene-vinyl acetate copolymer", Database WPI, AN 2013-G75464 (2013).

Vrbinc, Acta Chim. Slov., 54:254-267, 2007.

https://www.accessdata.fda.gov/drugsatfda_docs/label/2022/212304s000lbl.pdf.

* cited by examiner

SYSTEMS COMPRISING A COMPOSITE BACKING AND METHODS FOR LONG TERM TRANSDERMAL ADMINISTRATION

CROSS-REFERENCE TO RELATED APPLICATIONS

This application is a continuation of U.S. application Ser. No. 17/200,481, filed Mar. 12, 2021, which is a continuation of U.S. application Ser. No. 15/396,236, filed Dec. 30, 2016, now U.S. Pat. No. 10,966,936; which claims the benefit of U.S. Provisional Application No. 62/273,288, filed Dec. 30, 2015; and which also claims the benefit of U.S. Provisional Application No. 62/367,055, filed Jul. 26, 2016, all of which are incorporated herein by reference in their entireties.

TECHNICAL FIELD

The subject matter described herein relates to a transdermal delivery system comprising a backing for improved long term administration. The delivery system is suitable for prolonged administration of an active or therapeutic agent with improved adhesion to the skin at an administration site.

BACKGROUND

Transdermal delivery systems have become more desirable as they have the advantage of avoiding difficulties associated with gastrointestinal absorption of an active agent (e.g. effect of gastrointestinal pH and/or enzyme activity on the active agent, drug-food interactions, gastrointestinal side effects, eliminates pulsed entry into system circulation, and avoids high first-pass effect through the liver). Transdermal delivery systems may also increase patient compliance due to the ability for the patient to self-administer and avoids more invasive treatments such as injections. Transdermal delivery may advantageously provide controlled, constant delivery of the active agent, which may result in less fluctuation in circulating levels of the agent as compared to oral delivery.

Long term administration of transdermal patches is challenging, especially for patches that use occlusive backings. Most transdermal patches cannot remain adhered to the skin or other administration site for an extended period of time, e.g. at least or about 7 days. However, continuous contact of the patch with the patient's skin is necessary for proper drug delivery from the patch. The FDA lists problems associated with transdermal patches include the patch not flexing or conforming to the skin; the patch not sticking or the edges of the patch curling after 24 hours (www.fda.gov). Disadhesion may alter or prevent delivery of the drug from the patch. Friction between the layers of the patch and the administration site may cause the patch to buckle, wrinkle, and/or fail by losing contact with the skin. To address these problems, transdermal patches that are approved for long term use are of small size (e.g. less than 25 cm$^2$) such as the Catapres® or Ortho Evra® patches or require an over-sized overlay to cover the patch. The use of an overlay increases patch size and results in about a 2-3 fold increase in the total patch area. Therefore, use of an overlay is only practical for relatively small patches (e.g. not more than about 40 cm$^2$). Many of the multi-day use patch manufacturers recommend using medical tape to secure the patch. For example, the patient instructions for the fentanyl Duragesic® patch recommends applying first aid tape at the edges or use of adhesive dressings as a patch overlay to prevent the problem of patches that do not stick to the skin properly (see www.duragesic.com).

Another approach to long term transdermal patches is the use of a relatively breathable backing layer to increase wear time. Success with these patches is limited as the increased breathability of the backing layer reduces drug flux requiring an increase in total patch area.

Therefore, there exists a need for transdermal compositions, devices and methods that address at least these shortcomings.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

It is an object of the present invention to provide methods and compositions to effect long term or prolonged transdermal delivery of an active agent.

In a first aspect, a composite backing layer for use in a transdermal patch is provided. In embodiments, the composite backing layer comprises a first layer comprised of a polymer fabric or a polymer film having a stretchability of at least about 5% in at least one direction; a second layer comprised of one or more adhesive polymers; and a third layer comprised of one or more polymers. Typically, the first and second layers are in contact and the second and third layers are in contact.

In some embodiments, the polymer fabric or polymer film is comprised of one or more polymers selected from polyesters, polyethylenes, polypropylenes, polyvinylchloride, polyethylene vinyl acetate or copolymers thereof, and polyurethanes. In embodiments, the first layer is selected from a woven polymer fabric, a non-woven polymer fabric, a polymer laminate, and a polymer/metal laminate. In some embodiments, the first layer has a thickness of about 0.5-10 mil.

In embodiments, the second layer is an adhesive layer. In some embodiments, the adhesive layer is an adhesive tie layer. In some embodiments, the one or more polymers of the second layer has at least one of (i) a tensile strength of less than about 10 MPa and (ii) an elongation of at least about 50%. In embodiments, the one or more polymers of the second layer are selected from acrylates, acrylate copolymers, polyisobutylene, silicone, polystyrene butyl rubber, polyethylene vinyl acetate and copolymers thereof, and plasticized polymers. In some embodiments, one or more of the adhesive polymers of the second layer have a shear strength that is less or equal to about 1-25% of the tensile strength for the polymer. In embodiments, the second layer has a thickness of about 0.5-30 mil.

In some embodiments, the third layer is formed of an occlusive or substantially occlusive material. In some embodiments, the third layer is comprised of one or more polymers selected from polyethylene terephthalate (PET), polyethylenes, vinyl acetates or copolymers thereof, polypropylenes, nylon, polystyrenes, polyvinylchloride, polyurethanes, ethylene-vinyl acetate, copolymers thereof, or mixtures/blends thereof. In some embodiments, the third layer is comprised of a polyethylene terephthalate/ethylene-vinyl acetate laminate. In other embodiments, the third layer is comprised of a polyethylene terephthalate film. In some embodiments, the third layer has a thickness of about 1-40 mil. In embodiments, the third layer is attached to an adhesive drug layer comprising one or more drugs.

In embodiments, the first layer, second layer, and third layer are laminated. In some embodiments, at least the first layer or the third layer is at least partially cut.

In a second aspect, a transdermal patch for delivery of an active agent is provided. In embodiments, the transdermal patch comprises (a) a composite backing layer comprising: (i) a first layer comprised of a polymer fabric or a polymer film having a stretchability of at least about 5% in at least one direction; (ii) a second layer comprised one or more adhesive polymers; and (iii) a third layer comprised of one or more polymers, where the first layer, second layer, and third layers are arranged in contact as a composite; (b) an adhesive drug layer comprising the active agent; and (c) a release liner.

In embodiments, the first layer polymer fabric or polymer film is comprised of one or more polymers selected from polyesters, polyethylenes, polypropylenes, polyvinylchloride, polyethylene vinyl acetate or copolymers thereof, and polyurethanes. In embodiments, the first layer is selected from an occlusive polymer film, a polymer laminate, a polymer/metal laminate, a breathable polymer film, a woven polymer fabric and a non-woven polymer fabric. In some embodiments, the first layer has a thickness of about 0.5-10 mil.

In embodiments, the one or more polymers of the second layer are selected from acrylates, acrylate copolymers, polyisobutylene, silicone, polystyrene butyl rubber, polyethylene vinyl acetate and copolymers thereof, and plasticized polymers. In some embodiments, one or more of the adhesive polymers of the second layer have a shear strength that is less or equal to about 1-25% of the tensile strength for the polymer. In some embodiments, the second layer has a thickness of about 0.5-30 mil.

In some embodiments, the third layer is formed of an occlusive or substantially occlusive material. In some embodiments, the third layer is comprised of one or more polymers selected from polyethylene terephthalate (PET), polyethylenes, vinyl acetates or copolymers thereof, polypropylenes, nylon, polystyrenes, polyvinylchloride, polyurethanes, ethylene-vinyl acetate, copolymers thereof, or mixtures/blends thereof. In some embodiments, the third layer is comprised of a polyethylene terephthalate/ethylene-vinyl acetate laminate. In other embodiments, the third layer is comprised of a polyethylene terephthalate film. In embodiments, the third layer has a thickness of about 1-40 mil.

In embodiments, the release liner is formed of a material selected from a silicone coated polyethylene terephthalate, a fluorocarbon, a fluorocarbon coated polyethylene terephthalate, and a fluorosilicone coated polyethylene terephthalate.

In a further aspect, a method of transdermally administering an active agent is provided. In embodiments, the method comprises removing a release liner from the transdermal patch and adhering the transdermal patch to the skin of a patient for a period up to about 10 days to deliver the active agent to said patient.

In embodiments, the transdermal patch comprises (a) a composite backing layer, (b) an adhesive drug layer comprising the active agent; and (c) a release liner. In embodiments, the composite backing layer comprises a first layer comprised of a polymer fabric or a polymer film having a stretchability of at least about 5% in at least one direction; a second layer comprised one or more adhesive polymers; and a third layer comprised of one or more polymers. In embodiments, the first layer, second layer, and third layers are arranged in contact as a composite.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Figure 1:
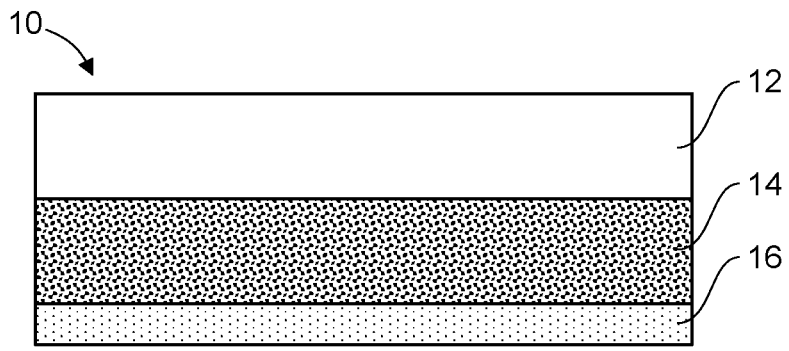
FIG. 1 is an illustration of a transdermal patch having a composite backing, an agent adhesive layer and a backing layer in accord with embodiments described herein.

Various aspects now will be described more fully hereinafter. Such aspects may, however, be embodied in many different forms and should not be construed as being limited to the embodiments set forth herein; rather, these embodiments are provided so that this disclosure will be thorough and complete, and will fully convey its scope to those skilled in the art.

It is to be understood that, unless otherwise indicated, these aspects and embodiments are not limited to specific polymers, oligomers, crosslinking agents, additives, manufacturing processes, or adhesive products. It is also to be understood that the terminology used herein is for the purpose of describing particular embodiments only, and is not intended to be limiting.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The use of terms of order or importance, including "first" and "second", is to distinguish and identify individual elements and does not denote or imply a particular order or importance unless clearly indicated by context.

The term "active agent" as used herein refers to a chemical material or compound suitable for topical or transdermal administration and that induces a desired effect. The terms include agents that are therapeutically effective, prophylactically effective, and cosmetically effective agents. The terms "active agent", "drug" and "therapeutic agent" are used interchangeably herein.

The term "hydrogel" is used in the conventional sense to refer to water-swellable polymeric matrices that can absorb a substantial amount of water to form elastic gels, wherein "matrices" are three-dimensional networks of macromolecules held together by covalent or noncovalent crosslinks. Upon placement in an aqueous environment, dry hydrogels swell to the extent allowed by the degree of cross-linking.

The term "hydrogel composition" refers to a composition that either contains a hydrogel or is entirely composed of a hydrogel. As such, "hydrogel compositions" encompass not only hydrogels per se but also compositions that not only contain a hydrogel but also contain one or more non-hydrogel components or compositions, e.g., hydrocolloids, which contain a hydrophilic component (which may contain or be a hydrogel) distributed in a hydrophobic phase.

"Matrix" as used herein refers to a solid or semi-solid substance including, but not limited to, a polymeric material, adhesive or gel. The matrix typically serves as a repository or carrier for substances including the therapeutic agent.

"Occlusive" as used herein refers to a material that limits the diffusion rate of moisture vapor and/or oxygen. A "non-occlusive" material allows a higher diffusion rate for moisture vapor and/or oxygen.

"Optional" or "optionally" means that the subsequently described circumstance may or may not occur, so that the description includes instances where the circumstance occurs and instances where it does not.

The term "skin" as used herein refers to skin or other biological membranes or mucosal tissue, including the interior surface of body cavities that have a mucosal lining. The term "skin" should be interpreted as including "mucosal tissue" and vice versa. It will be understood by persons of skill in the art that in most or all instances the same inventive principles apply to administration through other biological membranes such as those which line the interior of the mouth (e.g. oral mucosal membranes), gastro-intestinal tract, blood-brain barrier, or other body tissues or organs or biological membranes which are exposed or accessible during surgery or during procedures such as laparoscopy or endoscopy.

"Substantially" or "essentially" means nearly totally or completely, for instance, 90-95% or greater of some given quantity.

The term "therapeutically effective amount" as used herein refers to the amount of an active agent that is nontoxic but sufficient to provide the desired therapeutic effect. The amount that is "effective" will vary from subject to subject, depending on the age and general condition of the individual, the particular active agent or agents, and the like as known to those skilled in the art.

The terms "transdermal" or "transdermal delivery" as used herein refer to administration of an active agent to a body surface of an individual so that the agent passes through the body surface, e.g., skin, and into the individual's blood stream (systemic circulation). The term "transdermal" is intended to include transmucosal administration, i.e., administration of a drug to the mucosal (e.g., sublingual, buccal, vaginal, rectal) surface of an individual so that the agent passes through the mucosal tissue and into the individual's blood stream.

The terms "transdermal patch", "transdermal device" and/or "transdermal system" all relate to a layered patch, device or system that provides transdermal delivery of an active agent therefrom. The terms are used interchangeably herein.

II. Transdermal Devices and Systems

The systems and devices described herein are designed for prolonged or long term transdermal administration of an active agent. The compositions may be used in devices, patches or systems suitable for transdermal delivery of the active agent. Reference to a transdermal device, system or patch herein applies equally to each of the terms. The devices and systems are especially useful for long term delivery of the active agent from the device. For the long term delivery, the system must remain adhered or substantially adhered to the administration site as delivery of the active agent from the transdermal device requires contact between the agent containing layer and the administration site (directly or indirectly). Most transdermal patches cannot or do not remain sufficiently adhered to the skin for an extended period of more than a couple of days. Many commercial patches advise users to replace patches that peel off the skin or become substantially unadhered. The adhesion problem becomes greater for larger patch sizes and/or for patches that are applied for longer durations such as more than 1-3 days. Friction between moving skin and the static backing layer increases shear resistance of the adhesive/drug layer that is adhered to the stiff backing layer. These patches are either lifted off the skin or become buckled up from the skin, causing the patch to lose contact with the skin. Eventually, this results in patch failure. This friction may also lead to skin irritation, particularly along the edges of the patch. The propensity for larger patches to buckle or fail practically limits the size of patches. Because the patch size is one factor in the dose of the active agent that is delivered, the patch size may also limit the dose and duration of administration of the active agent.

The present transdermal devices and systems provide a transdermal device or system that includes a composite backing layer that reduces friction within the device or system and allows for long term wear, larger patch size, and/or reduced skin irritation.

In some embodiments, the transdermal device, patch or system is useful for long term or extended wear or administration. In embodiments, the transdermal device is suitable for administration of at least about 3 days or more. In some embodiments, the transdermal device is suitable for administration of at least about or up to about 3-14 days. In some embodiments, the transdermal device is suitable for administration up to about 10-14 days. In some embodiments, the transdermal device is suitable for administration of at least about or up to about 3-5 days, 3-7 days, 3-10 days, 5-7 days, 5-10 days, 5-14 days, 6-10 days, 6-14 days, 7-10 days, 7-14 days, 8-10 days, 8-14 days, 9-10 days, 9-14 days, or 10-14 days. In some non-limiting embodiments, the transdermal device is suitable for administration of at least about or up to about 3 days, 4 days, 5 days, 6 days, 7 days, 8 days, 9 days, 10 days, or 14 days. By suitable for administration, it is meant that the device, patch or system remains sufficiently adhered to the administration site to allow for contact of the adhesive drug layer with the skin such that the active agent is transdermally delivered. In embodiments, the device, patch or system is continuously adhered to the administration site. In some embodiments, the device, patch or system is substantially adhered to the administration site.

FIG. 1 shows an embodiment of an exemplary transdermal patch, device or system, generally designated at 10, having a composite backing layer or overlay. In this embodiment, the device includes a composite backing layer 12, an adhesive drug layer 14 and an optional release liner 16.

The backing layer provides a structural element for holding or supporting the adhesive drug layer. In the discussion of the backing layer below, it will be appreciated that the discussion applies to the backing layer as a whole as well as any one or more of the individual layers of the composite backing layer. The backing layer may be formed of any suitable material as known in the art. In some embodiments, the backing layer is occlusive or breathable. In some embodiments, the backing layer is preferably impermeable or substantially impermeable to moisture by preventing passage of all or substantially all moisture. In one exemplary embodiment, the barrier layer has an MVTR (moisture vapor transmission rate) of less than about 50 g/m$^2$/day. In some embodiments, the barrier layer has an MVTR of about 0.5-1500 g/m$^2$/day or about 0.5-50 g/m$^2$/day. In some specific but not limiting embodiments, the barrier layer has an MVTR of less than about or about 0.5 g/m$^2$/day, 1 g/m$^2$/day, 5 g/m$^2$/day, 10 g/m$^2$/day, 15 g/m$^2$/day, 20 g/m$^2$/day, 25 g/m$^2$/day, 30 g/m$^2$/day, 40 g/m$^2$/day, or 50 g/m$^2$/day. In some embodiments, the backing layer is preferably inert and/or does not absorb components of the adhesive drug layer, including the active agent. In some embodiments, the backing layer preferably prevents release of components of the adhesive drug layer through the backing layer. The backing layer may be flexible, substantially flexible or nonflexible. The backing layer is preferably at least partially flexible such that the backing layer is able to conform at least partially to the shape of the skin where the patch is applied. In some embodiments, the backing layer is flexible such that the backing layer conforms to the shape of the skin where the patch is applied. In some embodiments, the backing layer is sufficiently flexible to maintain contact at the application site with movement, e.g. skin movement. Typically, at least some of the materials used for the backing layer should permit the device to follow the contours of the skin or other application site and be worn comfortably on areas of skin such as at joints or other points of flexure, that are normally subjected to mechanical strain with little or no likelihood of the device disengaging from the skin due to differences in the flexibility or resiliency of the skin and the device. In some embodiments, the backing layer does not affect and/or control the release profile of the active agent from the device. In some embodiments, the backing layer is not the predominant factor affecting and/or controlling the release profile of the active agent from the device.

In some embodiments, at least a portion of the transdermal patch has a size or surface area of about 5-200 cm$^2$. In some non-limiting embodiments, the transdermal patch has a size or surface area of about 5-10 cm$^2$, 5-15 cm$^2$, 5-20 cm$^2$, 5-25 cm$^2$, 5-30 cm$^2$, 5-40 cm$^2$, 5-45 cm$^2$, 5-50 cm$^2$, 5-60 cm$^2$, 5-70 cm$^2$, 5-75 cm$^2$, 5-80 cm$^2$, 5-90 cm$^2$, 5-100 cm$^2$, 5-125 cm$^2$, 5-150 cm$^2$, 5-175 cm$^2$, 10-15 cm$^2$, 10-20 cm$^2$, 10-25 cm$^2$, 10-30 cm$^2$, 10-40 cm$^2$, 10-45 cm$^2$, 10-50 cm$^2$, 10-60 cm$^2$, 10-70 cm$^2$, 10-75 cm$^2$, 10-80 cm$^2$, 10-90 cm$^2$, 10-100 cm$^2$, 10-125 cm$^2$, 10-150 cm$^2$, 10-175 cm$^2$, 10-200 cm$^2$, 15-20 cm$^2$, 15-25 cm$^2$, 15-30 cm$^2$, 15-40 cm$^2$, 15-45 cm$^2$, 15-50 cm$^2$, 15-60 cm$^2$, 15-70 cm$^2$, 15-75 cm$^2$, 15-80 cm$^2$, 15-90 cm$^2$, 15-100 cm$^2$, 15-125 cm$^2$, 15-150 cm$^2$, 15-175 cm$^2$, 15-200 cm$^2$, 20-25 cm$^2$, 20-30 cm$^2$, 20-40 cm$^2$, 20-45 cm$^2$, 20-50 cm$^2$, 20-60 cm$^2$, 20-70 cm$^2$, 20-75 cm$^2$, 20-80 cm$^2$, 20-90 cm$^2$, 20-100 cm$^2$, 20-125 cm$^2$, 20-150 cm$^2$, 20-175 cm$^2$, 20-200 cm$^2$, 25-30 cm$^2$, 25-40 cm$^2$, 25-45 cm$^2$, 25-50 cm$^2$, 25-60 cm$^2$, 25-70 cm$^2$, 25-75 cm$^2$, 25-80 cm$^2$, 25-90 cm$^2$, 25-100 cm$^2$, 25-125 cm$^2$, 25-150 cm$^2$, 25-175 cm$^2$, 25-200 cm$^2$, 30-40 cm$^2$, 30-45 cm$^2$, 30-50 cm$^2$, 30-60 cm$^2$, 30-70 cm$^2$, 30-75 cm$^2$, 30-80 cm$^2$, 30-90 cm$^2$, 30-100 cm$^2$, 30-125 cm$^2$, 30-150 cm$^2$, 30-175 cm$^2$, 30-200 cm$^2$, 40-45 cm$^2$, 40-50 cm$^2$, 40-60 cm$^2$, 40-70 cm$^2$, 40-75 cm$^2$, 40-80 cm$^2$, 40-90 cm$^2$, 40-100 cm$^2$, 40-125 cm$^2$, 40-150 cm$^2$, 40-175 cm$^2$, 40-200 cm$^2$, 45-50 cm$^2$, 45-60 cm$^2$, 45-70 cm$^2$, 45-75 cm$^2$, 45-80 cm$^2$, 45-90 cm$^2$, 45-100 cm$^2$, 45-125 cm$^2$, 45-150 cm$^2$, 45-175 cm$^2$, 45-200 cm$^2$, 50-60 cm$^2$, 50-70 cm$^2$, 50-75 cm$^2$, 50-80 cm$^2$, 50-90 cm$^2$, 50-100 cm$^2$, 50-125 cm$^2$, 50-150 cm$^2$, 50-175 cm$^2$, 50-200 cm$^2$, 60-70 cm$^2$, 60-75 cm$^2$, 60-80 cm$^2$, 60-90 cm$^2$, 60-100 cm$^2$, 60-125 cm$^2$, 60-150 cm$^2$, 60-175 cm$^2$, 60-200 cm$^2$, 70-75 cm$^2$, 70-80 cm$^2$, 70-90 cm$^2$, 70-100 cm$^2$, 70-125 cm$^2$, 70-150 cm$^2$, 70-175 cm$^2$, 70-200 cm$^2$, 80-90 cm$^2$, 80-100 cm$^2$, 80-125 cm$^2$, 80-150 cm$^2$, 80-175 cm$^2$, 80-200 cm$^2$, 90-100 cm$^2$, 90-125 cm$^2$, 90-150 cm$^2$, 90-175 cm$^2$, 90-200 cm$^2$, 100-125 cm$^2$, 100-150 cm$^2$, 100-175 cm$^2$, 100-200 cm$^2$, 125-150 cm$^2$, 125-175 cm$^2$, 125-200 cm$^2$, 150-175 cm$^2$, 150-200 cm$^2$, or 175-200 cm$^2$. In specific, but not limiting, embodiments, the transdermal patch has a size or surface area of about 5 cm$^2$, 10 cm$^2$, 15 cm$^2$, 20 cm$^2$, 25 cm$^2$, 30 cm$^2$, 40 cm$^2$, 45 cm$^2$, 50 cm$^2$, 60 cm$^2$, 70 cm$^2$, 75 cm$^2$, 80 cm$^2$, 90 cm$^2$, 100 cm$^2$, 125 cm$^2$, 150 cm$^2$, 175 cm$^2$, or 200 cm$^2$. It will be appreciated that different layers of the backing and/or the device may have a different surface area or size. In one embodiment, at least a portion (e.g. at least one layer) of the backing extends beyond the edge of at least the adhesive drug layer.

The transdermal patch may be prepared to have a thickness such that the desired amount of drug formulation is contained within the patch including the desired components while maintaining a thickness that is wearable and comfortable for the subject. In some embodiments, the transdermal patch has a thickness of about 2-200 mil including the composite backing layer and the adhesive drug layer. In specific non-limiting embodiments, the transdermal patch has a thickness of about 2-10 mil, 2-25 mil, 2-30 mil, 2-40 mil, 2-50 mil, 2-75 mil, 2-80 mil, 2-100 mil, 2-125 mil, 2-150 mil, 2-175 mil, 2.5-10 mil, 2.5-25 mil, 2.5-30 mil, 2.5-40 mil, 2.5-50 mil, 2.5-75 mil, 2.5-80 mil, 2.5-100 mil, 2.5-125 mil, 2.5-150 mil, 2.5-175 mil, 2.5-200 mil, 3-10 mil, 3-25 mil, 3-30 mil, 3-40 mil, 3-50 mil, 3-75 mil, 3-80 mil, 3-100 mil, 3-125 mil, 3-150 mil, 3-175 mil, 3-200 mil, 5-10 mil, 5-25 mil, 5-30 mil, 5-40 mil, 5-50 mil, 5-75 mil, 5-80 mil, 5-100 mil, 5-125 mil, 5-150 mil, 5-175 mil, 5-200 mil, 7-10 mil, 7-25 mil, 7-30 mil, 7-40 mil, 7-50 mil, 7-75 mil, 7-80 mil, 7-100 mil, 7-125 mil, 7-150 mil, 7-175 mil, 7-200 mil, 8-10 mil, 8-25 mil, 8-30 mil, 8-40 mil, 8-50 mil, 8-75 mil, 8-80 mil, 8-100 mil, 8-125 mil, 8-150 mil, 8-175 mil, 8-200 mil, 10-25 mil, 10-30 mil, 10-40 mil, 10-50 mil, 10-75 mil, 10-80 mil, 10-100 mil, 10-125 mil, 10-150 mil, 10-175 mil, 10-200 mil, 25-30 mil, 25-40 mil, 25-50 mil, 25-75 mil, 25-80 mil, 25-100 mil, 25-125 mil, 25-150 mil, 25-175 mil, 25-200 mil, 30-40 mil, 30-50 mil, 30-75 mil, 30-80 mil, 30-100 mil, 30-125 mil, 30-150 mil, 30-175 mil, 30-200 mil, 40-50 mil, 40-75 mil, 40-80 mil, 40-100 mil, 40-125 mil, 40-150 mil, 40-175 mil, 40-200 mil, 50-75 mil, 50-80 mil, 50-100 mil, 50-125 mil, 50-150 mil, 50-175 mil, 50-200 mil, 75-80 mil, 75-100 mil, 75-125 mil, 75-150 mil, 75-175 mil, 75-200 mil, 80-100 mil, 80-125 mil, 80-150 mil, 80-175 mil, 80-200 mil, 100-125 mil, 100-150 mil, 100-175 mil, 100-200 mil, 125-150 mil, 125-175 mil, 125-200 mil, 150-175 mil, 150-200 mil, or 175-200 mil. In specific, but not limiting, embodiments, the transdermal patch has a thickness of about 2 mil, 2.5 mil, 3 mil, 4 mil, 5 mil, 7 mil, 7.5 mil, 8 mil, 10 mil, 15 mil, 20 mil, 25 mil, 30 mil, 40 mil, 50 mil, 60 mil, 70 mil, 75 mil, 80 mil, 90 mil, 100 mil, 125 mil, 150 mil, 175 mil, or 200 mil. The thickness for the patch describes above may apply to the patch including the optional release liner or the patch as applied (including only the backing and drug layers).

Figure 2:
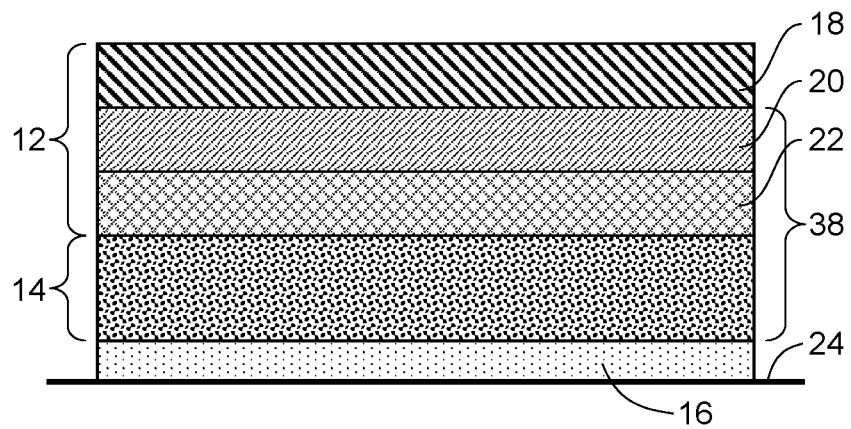
FIG. 2 is an illustration of a transdermal patch comprising a layered composite backing in accord with embodiments described herein.
Figure 3:
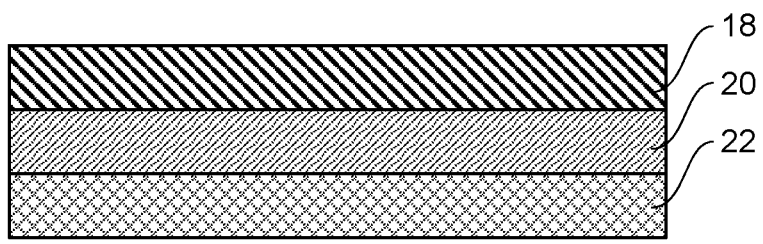
FIG. 3 is an illustration of a composite backing in accord with embodiments described herein.

In a first aspect, as seen in FIGS. 2 and 3, the backing layer or overlay 12 is a composite comprising multiple or several layers to allow movement within the composite backing/and or the adhesive drug layer 14. The composite layers may be laminated or otherwise adhered as known in the art. Lamination generally refers to manufacture by layering and adhering materials. In embodiments as shown in FIG. 3, the backing layer comprises a first exterior or top layer 18, a second, middle layer 20, and a third or bottom layer 22. In the embodiment as shown in FIG. 2, at least the second/middle layer 20 and the third/bottom layer 22 of the composite backing as well as the adhesive/drug layer 14, collectively indicated at 38, allow for shear yield and/or movement to allow dissipation of movement within the transdermal delivery system. In other embodiments, at least the first/top layer 18 and the second/middle layer 20 of the composite backing allow for shear yield and/or movement to allow dissipation of movement within the transdermal delivery system.

In non-limiting embodiments, the composite layer has a thickness of about 2-100 mil. In specific non-limiting embodiments, the composite layer has a thickness of about 5-10 mil, 5-15 mil, 5-20 mil, 5-25 mil, 5-30 mil, 5-40 mil, 5-50 mil, 5-60 mil, 5-70 mil, 5-75 mil, 5-80 mil, 5-90 mil, 5-100 mil, 10-15 mil, 10-20 mil, 10-25 mil, 10-30 mil, 10-40 mil, 10-50 mil, 10-60 mil, 10-70 mil, 10-75 mil, 10-80 mil, 10-90 mil, 10-100 mil, 15-20 mil, 15-25 mil, 15-30 mil, 15-40 mil, 15-50 mil, 15-60 mil, 15-70 mil, 15-75 mil, 15-80 mil, 15-90 mil, 15-100 mil, 20-25 mil, 20-30 mil, 20-40 mil, 20-50 mil, 20-60 mil, 20-70 mil, 20-75 mil, 20-80 mil, 20-90 mil, 20-100 mil, 25-30 mil, 25-40 mil, 25-50 mil, 25-60 mil, 25-70 mil, 25-75 mil, 25-80 mil, 25-90 mil, 25-100 mil, 30-40 mil, 30-50 mil, 30-60 mil, 30-70 mil, 30-75 mil, 30-80 mil, 30-90 mil, 30-100 mil, 40-50 mil, 40-60 mil, 40-70 mil, 40-75 mil, 40-80 mil, 40-90 mil, 40-100 mil, 50-60 mil, 50-70 mil, 50-75 mil, 50-80 mil, 50-90 mil, 50-100 mil, 50-70 mil, 50-75 mil, 50-80 mil, 50-90 mil, 50-100 mil, 60-70 mil, 60-75 mil, 60-80 mil, 60-90 mil, 60-100 mil, 70-75 mil, 70-80 mil, 70-90 mil, 70-100 mil, 75-80 mil, 75-90 mil, 75-100 mil, 80-90 mil, 80-100 mil, or 90-100 mil.

The first layer is a protective outer layer which serves at least to protect the patch. In some embodiments, the first layer overlays or overhangs at least one edge of at least one of the second layer, third layer, or the adhesive/drug layer. In embodiments, the first layer is comprised of a woven or non-woven polymer fabric, a polymer film, an occlusive polymer film, a polymer laminate and a polymer/metal laminate. A woven fabric is generally produced from warp and weft polymeric or natural fibers. Exemplary woven or non-woven fabrics are polyester fabrics. One exemplary woven fabric is a bi-elastic polyester fabric such as the KOB 053 available from Karl Otto GmbH & Co. In some embodiments, the polymer film is an elastic polymer film. In some embodiments, the first layer is comprised of stretchable polymers. In some embodiments, the first layer is comprised of one or more polymers having a low shear strength or resistance. The shear strength may be measured by any methods as known in the art. Some exemplary methods of testing or measuring shear strength include the punch technique or test and the Iosipescu test as known to those skilled in the art. In some embodiments, the shear strength may be measured using a viscometer.

Suitable polymers are known in the art and include elastomers, polyesters, polyethylenes, polypropylenes, polyurethanes polyether amides and copolymers thereof. In some embodiments, the polymer is polyethylene vinyl acetate, polyvinylchloride or copolymers thereof. In some embodiments, the first layer is comprised of one or more of polyethylene terephthalate, polyvinyl acetate, polyvinylidene chloride, polyvinylchloride, and polyethylene vinyl acetate or copolymers thereof. Polymer/metal laminates are known in the art and include aluminum laminates and tin laminates, among others. In some embodiments, the first layer is comprised of a laminate. In one non-limiting embodiment, the first layer is comprised of a polyethylene and polyester laminate such as the laminate sold under the name Scotchpak™ #9723. In some embodiments, the first layer is formed of a polyurethane film, a thermoplastic polyester elastomer such as a Hytrel® film available from DuPont®, or a polyethylene vinyl acetate film. In some embodiments, at least the first layer of the backing layer is occlusive.

In some embodiments, the first layer is a stretchable, elastic and/or flexible layer comprised of one or more polymers having a stretchability and/or elasticity of at least about 5% in at least one direction. In this embodiment, the first layer, along with the second or middle layer absorbs the stress of the movement of the adhesive drug layer or device against the skin or other administration site. In some embodiments, the first layer is comprised of one or more stretchable polymers having a stretchability and/or elasticity of at least about 5% or at least about 10% in at least one direction. The stretchability may be ascertained by any suitable means as known in the art. In some embodiments, the stretchability is determined at room temperature or at approximately 20-25° C. In embodiments, the first layer is comprised of one or more stretchable polymers having a stretchability and/or elasticity of at least about 5-50%. In some embodiments, the first layer is comprised of one or more stretchable polymers having a stretchability and/or elasticity of at least about 5-40%, 5-30%, 5-25%, 5-20%, 5-15%, 5-10%, 10-50%, 10-40%, 10-30%, 10-25%, 10-20%, 10-15%, 15-50%, 15-40%, 15-30%, 15-25%, 15-20%, 20-50%, 20-40%, 20-30%, 20-25%, 25-50%, 25-40%, 25-30%, 30-50%, 30-40%, or 40-50%. In specific, but not limiting embodiments, the first layer is comprised of one or more stretchable polymers having a stretchability and/or elasticity of at least about 5%, 10%, 15%, 20%, 25%, 30%, 40%, or 50%. In some embodiments, the first layer is stretchable, but not elastic. In other embodiments, the first layer is relatively stiff.

In embodiments, the first layer has a thickness of about 0.5-15 mil. In non-limiting embodiments, the first layer has a thickness of between about 0.5-0.75 mil, 0.5-1 mil, 0.5-1.5 mil, 0.5-2 mil, 0.5-2.5 mil, 0.5-3 mil, 0.5-4 mil, 0.5-5 mil, 0.5-6 mil, 0.5-7 mil, 0.5-8 mil, 0.5-9 mil, 0.5-10 mil, 0.75-1 mil, 0.75-1.5 mil, 0.75-2 mil, 0.75-2.5 mil, 0.75-3 mil, 0.75-4 mil, 0.75-5 mil, 0.75-6 mil, 0.75-7 mil, 0.75-8 mil, 0.75-9 mil, 0.75-10 mil, 0.75-15 mil, 1-1.5 mil, 1-2 mil, 1-2.5 mil, 1-3 mil, 1-4 mil, 1-5 mil, 1-6 mil, 1-7 mil, 1-8 mil, 1-9 mil, 1-10 mil, 1-15 mil, 1.5-2 mil, 1.5-2.5 mil, 1.5-3 mil, 1.5-4 mil, 1.5-5 mil, 1.5-6 mil, 1.5-7 mil, 1.5-8 mil, 1.5-9 mil, 1.5-10 mil, 1.5-15 mil, 2-2.5 mil, 2-3 mil, 2-4 mil, 2-5 mil, 2-6 mil, 2-7 mil, 2-8 mil, 2-9 mil, 2-10 mil, 2-15 mil, 2.5-3 mil, 2.5-4 mil, 2.5-5 mil, 2.5-6 mil, 2.5-7 mil, 2.5-8 mil, 2.5-9 mil, 2.5-10 mil, 2.5-15 mil, 3-4 mil, 3-5 mil, 3-6 mil, 3-7 mil, 3-8 mil, 3-9 mil, 3-10 mil, 3-15 mil, 4-5 mil, 4-6 mil, 4-7 mil, 4-8 mil, 4-9 mil, 4-10 mil, 4-15 mil, 5-6 mil, 5-7 mil, 5-8 mil, 5-9 mil, 5-10 mil, 5-15 mil, 6-7 mil, 6-8 mil, 6-9 mil, 6-10 mil, 6-15 mil, 7-8 mil, 7-9 mil, 7-10 mil, 7-15 mil, 8-9 mil, 8-10 mil, 8-15 mil, 9-10 mil, 9-15 mil or 10-15 mil. In specific non-limiting embodiments, the first layer has a thickness of about 0.5 mil, 0.75 mil, 1 mil, 1.5 mil, 2 mil, 3 mil, 4 mil, 5 mil, 6 mil, 7 mil, 8 mil, 9 mil, 10 mil or 15 mil.

The composite backing layer further comprises a second or middle layer 20 adjacent the first or top layer. The second layer is preferably an adhesive, tie or binding layer positioned between the first and third layers. The second layer serves to adhere, attach or bind the first and third layers. In embodiments, one of the first or third layers is relatively stiff and/or stationary and the other of the first and third layer is flexible and/or elastic. The second layer, along with the flexible or relatively flexible layer absorbs the stress of the adhesive drug layer against the skin or other administration site. In embodiments, the second layer is comprised of polymers having a tensile or yield strength of less than about 5 MPa or about 10 MPa. The tensile strength is a measurement of the force required per unit area (MPa) at the break point of the polymer. In some embodiments, the second layer is comprised of one or more polymers having a tensile strength of less than about 5-10 MPa. In some embodiments, the second layer is comprised of one or more polymers having a tensile strength of less than about 6-10 MPa, 7-10 MPa, 8-10 MPa, or 9-10 MPa. In some embodiments, the second layer is comprised of polymers such that the second layer as a whole has a tensile strength of less than about 10 MPa. The tensile or yield strength may be ascertained by any suitable means as known in the art. In one embodiment, the tensile or yield strength is determined by the ASTM D882 test which comprising pulling a polymer sample from both ends to determine the force required at the yield or break point. In some embodiments, the tensile strength is the tensile strength at room temperature or at approximately 20-25° C.

In embodiments, the second layer is comprised of polymers having an elongation of not less than or at least about 10%. In some embodiments, the second layer is comprised of polymers having an elongation of not less than or at least about 50%. The elongation refers to the percentage of elongation before the polymer breaks under an applied strain. In embodiments, the % elongation is the final length (L) of the polymer or polymer material after stretching, minus the initial length (Li) divided by the initial length. The % elongation may be ascertained by any suitable means as known in the art. In some embodiments, the % elongation is determined at room temperature or at approximately 20-25° C. In some embodiments, the second layer is comprised of polymers such that the second layer as a whole has a % elongation of at least about or not less than about 10% or about 50%. In some embodiments, the second layer is comprised of one or more polymers having a % elongation of at least about 10-500%. In some embodiments, the second layer is comprised of one or more polymers having a % elongation of at least about 10-75%, 10-100%, 10-150%, 10-200%, 10-250%, 10-300%, 10-400%, 50-75%, 50-100%, 50-150%, 50-200%, 50-250%, 50-300%, 50-400%, 50-500%, 75-100%, 75-150%, 75-200%, 75-250%, 75-300%, 75-400%, 75-500%, 100-150%, 100-200%, 100-250%, 100-300%, 100-400%, 100-500%, 150-200%, 150-250%, 150-300%, 150-400%, 150-500%, 200-250%, 200-300%, 200-400%, 200-500%, 250-300%, 250-400%, 250-500%, 300-400%, 300-500%, 400-500% or more.

In some embodiments, the second layer is comprised of one or more polymers having a low shear strength. Shear strength refers to the polymer's ability to resist forces that cause the internal structure to slide against itself. In some embodiments, the shear strength is expressed in terms of a percentage of the tensile strength of the polymer(s). In some non-limiting embodiments, one or more of the polymers of the second layer have a shear strength that is or is less than about 1-25% of its tensile strength. In some embodiments, one or more of the polymers has a shear strength that is or is less than about 1-20%, 1-15%, 1-10%, 1-5%, 5-25%, 5-20%, 5-15%, 5-10%, 10-25%, 10-20%, 10-15%, 15-25%, 15-20%, or 20-25% of the tensile strength for the polymer. In some specific, but not limiting embodiments, one or more of the polymers has a shear strength that is or is less than about 1%, 5%, 10%, 15%, 20%, 25%, 30%, or 40% of the tensile strength for the polymer. In some embodiments, the shear strength is about or less than about 0.1-15 MPa. In some embodiments, the shear strength is about or less than about 0.1-10 MPa, 0.1-9 MPa, 0.1-8 MPa, 0.1-7 MPa, 0.1-6 MPa, 0.1-5 MPa, 0.1-4 MPa, 0.1-3 MPa, 0.1-2 MPa, 0.1-1 MPa, 0.1-0.5 MPa, 0.5-15 MPa, 0.5-10 MPa, 0.5-9 MPa, 0.5-8 MPa, 0.5-7 MPa, 0.5-6 MPa, 0.5-5 MPa, 0.5-4 MPa, 0.5-3 MPa, 0.5-2 MPa, 0.5-1 MPa, 1-15 MPa, 1-10 MPa, 1-9 MPa, 1-8 MPa, 1-7 MPa, 1-6 MPa, 1-5 MPa, 1-4 MPa, 1-3 MPa, 1-2 MPa, 2-15 MPa, 2-10 MPa, 2-9 MPa, 2-8 MPa, 2-7 MPa, 2-6 MPa, 2-5 MPa, 2-4 MPa, 2-3 MPa, 3-15 MPa, 3-10 MPa, 3-9 MPa, 3-8 MPa, 3-7 MPa, 3-6 MPa, 3-5 MPa, 3-4 MPa, 4-15 MPa, 4-10 MPa, 4-9 MPa, 4-8 MPa, 4-7 MPa, 4-6 MPa, 4-5 MPa, 5-15 MPa, 5-10 MPa, 5-9 MPa, 5-8 MPa, 5-7 MPa, 5-6 MPa, 6-15 MPa, 6-10 MPa, 6-9 MPa, 6-8 MPa, 6-7 MPa, 7-15 MPa, 7-10 MPa, 7-9 MPa, 7-8 MPa, 8-15 MPa, 8-10 MPa, 8-9 MPa, 9-15 MPa, 9-10 MPa, or 10-15 MPa.

In embodiments, the second layer is an adhesive layer. In some embodiments, the second layer is an adhesive tie layer.

In embodiments, the one or more polymers are selected from acrylates and acrylate copolymers, polyisobutylenes, silicone, polystyrene butyl rubber, polyethylene vinyl acetate and copolymers thereof. In some embodiments, the second layer is comprised of an adhesive selected from acrylic adhesives, polyisobutylene adhesives, or silicone adhesives. In some embodiments, the adhesive is a pressure sensitive adhesive. In some embodiments, the second layer is comprised of plasticized polymers.

In embodiments, the second layer has a thickness of about 0.5-30 mil. In non-limiting embodiments, the second layer has a thickness of between about 0.5-0.75 mil, 0.5-1 mil, 0.5-1.5 mil, 0.5-2 mil, 0.5-2.5 mil, 0.5-3 mil, 0.5-4 mil, 0.5-5 mil, 0.5-6 mil, 0.5-7 mil, 0.5-8 mil, 0.5-9 mil, 0.5-10 mil, 0.5-15 mil, 0.5-20 mil, 0.5-25 mil, 0.75-1 mil, 0.75-1.5 mil, 0.75-2 mil, 0.75-2.5 mil, 0.75-3 mil, 0.75-4 mil, 0.75-5 mil, 0.75-6 mil, 0.75-7 mil, 0.75-8 mil, 0.75-9 mil, 0.75-10 mil, 0.75-15 mil, 0.75-20 mil, 0.75-25 mil, 0.75-30 mil, 1-1.5 mil, 1-2 mil, 1-2.5 mil, 1-3 mil, 1-4 mil, 1-5 mil, 1-6 mil, 1-7 mil, 1-8 mil, 1-9 mil, 1-10 mil, 1-15 mil, 1-20 mil, 1-25 mil, 1-30 mil, 1.5-2 mil, 1.5-2.5 mil, 1.5-3 mil, 1.5-4 mil, 1.5-5 mil, 1.5-6 mil, 1.5-7 mil, 1.5-8 mil, 1.5-9 mil, 1.5-10 mil, 1.5-15 mil, 1.5-20 mil, 1.5-25 mil, 1.5-30 mil, 2-2.5 mil, 2-3 mil, 2-4 mil, 2-5 mil, 2-6 mil, 2-7 mil, 2-8 mil, 2-9 mil, 2-10 mil, 2-15 mil, 2-20 mil, 2-25 mil, 2-30 mil, 2.5-3 mil, 2.5-4 mil, 2.5-5 mil, 2.5-6 mil, 2.5-7 mil, 2.5-8 mil, 2.5-9 mil, 2.5-10 mil, 2.5-15 mil, 2.5-20 mil, 2.5-25 mil, 2.5-30 mil, 3-4 mil, 3-5 mil, 3-6 mil, 3-7 mil, 3-8 mil, 3-9 mil, 3-10 mil, 3-15 mil, 3-20 mil, 3-25 mil, 3-30 mil, 4-5 mil, 4-6 mil, 4-7 mil, 4-8 mil, 4-9 mil, 4-10 mil, 4-15 mil, 4-20 mil, 4-25 mil, 4-30 mil, 5-4 mil, 5-5 mil, 5-6 mil, 5-7 mil, 5-8 mil, 5-9 mil, 5-10 mil, 5-15 mil, 5-20 mil, 5-25 mil, 5-30 mil, 6-7 mil, 6-8 mil, 6-9 mil, 6-10 mil, 6-15 mil, 6-20 mil, 6-25 mil, 6-30 mil, 7-8 mil, 7-9 mil, 7-10 mil, 7-15 mil, 7-20 mil, 7-25 mil, 7-30 mil, 8-9 mil, 8-10 mil, 8-15 mil, 8-20 mil, 8-25 mil, 8-30 mil, 9-10 mil, 9-15 mil, 9-20 mil, 9-25 mil, 9-30 mil, 10-15 mil, 10-20 mil, 10-25 mil, 10-30 mil, 15-20 mil, 15-25 mil, 15-30 mil, 20-25 mil, 20-30 mil, or 25-30 mil. In specific non-limiting embodiments, the second layer has a thickness of about 0.5 mil, 0.75 mil, 1 mil, 1.5 mil, 2 mil, 3 mil, 4 mil, 5 mil, 6 mil, 7 mil, 8 mil, 9 mil, 10 mil, 15 mil, 20 mil, 25 mil, or 30 mil.

The composite backing layer further comprises a third or bottom layer adjacent the second or middle layer. In some embodiments, the third layer is a stretchable and/or flexible layer. In embodiments, the third layer, along with the second or middle layer absorbs the stress of the movement of the adhesive drug layer against the skin or other administration site. In some embodiments, the third layer is comprised of one or more stretchable polymers having a stretchability and/or elasticity of at least about 5% or at least about 10% in at least one direction. The stretchability may be ascertained by any suitable means as known in the art. In some embodiments, the stretchability is determined at room temperature or at approximately 20-25° C. In embodiments, the third layer is comprised of one or more stretchable polymers having a stretchability or elasticity of at least about 5-50%. In some embodiments, the third layer is comprised of one or more stretchable polymers having a stretchability or elasticity of at least about 5-40%, 5-30%, 5-25%, 5-20%, 5-15%, 5-10%, 10-50%, 10-40%, 10-30%, 10-25%, 10-20%, 10-15%, 15-50%, 15-40%, 15-30%, 15-25%, 15-20%, 20-50%, 20-40%, 20-30%, 20-25%, 25-50%, 25-40%, 25-30%, 30-50%, 30-40%, or 40-50%. In specific, but not limiting embodiments, the third layer is comprised of one or more stretchable polymers having a stretchability or elasticity of at least about 5%, 10%, 15%, 20%, 25%, 30%, 40%, or 50%.

In other embodiments, the third layer is relatively stiff as compared to at least one of the first or second layers.

In some embodiments, the third layer is occlusive or substantially occlusive. In other embodiments, the third layer is breathable.

In embodiments, the third layer has a thickness of about 1-40 mil. In non-limiting embodiments, the third layer has a thickness of between about 1-1.5 mil, 1-2 mil, 1-3 mil, 1-4 mil, 1-5 mil, 1-10 mil, 1-15 mil, 1-20 mil, 1-25 mil, 1-30 mil, 1-35 mil, 1.5-2 mil, 1.5-3 mil, 1.5-4 mil, 1.5-5 mil, 1.5-10 mil, 1.5-15 mil, 1.5-20 mil, 1.5-25 mil, 1.5-30 mil, 1.5-35 mil, 1.5-40 mil, 2-3 mil, 2-4 mil, 2-5 mil, 2-10 mil, 2-15 mil, 2-20 mil, 2-25 mil, 2-30 mil, 2-35 mil, 2-40 mil, 3-4 mil, 3-5 mil, 3-10 mil, 3-15 mil, 3-20 mil, 3-25 mil, 3-30 mil, 3-35 mil, 3-40 mil, 4-5 mil, 4-10 mil, 4-15 mil, 4-20 mil, 4-25 mil, 4-30 mil, 4-35 mil, 4-40 mil, 5-10 mil, 5-15 mil, 5-20 mil, 5-25 mil, 5-30 mil, 5-35 mil, 5-40 mil, 10-15 mil, 10-20 mil, 10-25 mil, 10-30 mil, 10-35 mil, 10-40 mil, 15-20 mil, 15-25 mil, 15-30 mil, 15-35 mil, 15-40 mil, 20-25 mil, 20-30 mil, 20-35 mil, 20-40 mil, 25-30 mil, 25-35 mil, 25-40 mil, 30-35 mil, 30-40 mil, or 35-40 mil. In specific, but not limiting embodiments, the third layer has a thickness of about 1 mil, 1.5 mil, 2 mil, 3 mil, 4 mil, 5 mil, 10 mil, 15 mil, 20 mil, 25 mil, 30 mil, 35 mil, or 40 mil.

In embodiments, the third layer is a non-woven or woven fabric formed of synthetic or natural fibers. In embodiments, the synthetic fibers are comprised of one or more polymer fibers. In embodiments, the natural fibers are comprised of at least one of cotton or silk. In other embodiments, the third layer is a polymer film, polymer laminate, or polymer matrix. In embodiments, the polymer is selected from one or more of polyesters such as polyethylene terephthalate (PET), polyethylenes, vinyl acetates or copolymers thereof, polypropylenes, nylon, polystyrenes, polyvinylchloride, polyurethanes, ethylene-vinyl acetate, copolymers thereof, or mixtures/blends thereof. In embodiments, the third layer is a polymer film comprised of a polyethylene terephthalate/ethylene-vinyl acetate laminate. In other embodiments, the third layer is comprised of polyethylene terephthalate. The third layer is attached or affixed to an adhesive/drug layer using any suitable means. In some embodiments, the third layer is affixed or attached to the adhesive/drug layer using a suitable adhesive.

Example 1 describes preparation of an exemplary transdermal delivery system comprising a composite backing layer. A stretchable or flexible polymer layer is laminated onto an occlusive backing using an adhesive. An adhesive formulation is prepared, coated onto a release liner and the formulation is laminated onto the polymer side of the composite backing laminate. Example 4 describes preparation of a further exemplary transdermal delivery system comprising a composite backing layer. A stretchable, woven fabric is laminated onto a polymer film using an adhesive. An adhesive drug formulation is prepared, coated onto a release liner and the formulation is laminated onto the polymer film side of the composite backing laminate.

Figure 5:
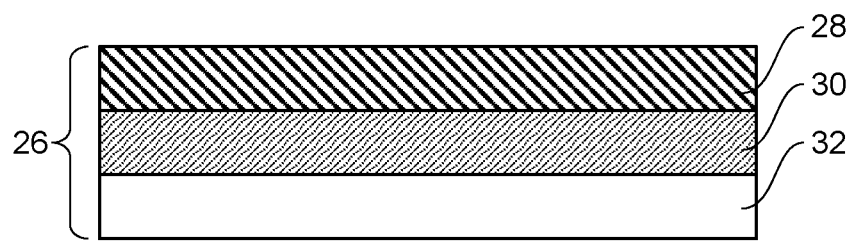
FIG. 5 is a side view illustrating an exemplary composite backing comprising separate pieces for a first or top layer.

In a second aspect, one or more layers of the composite backing is at least partially cut, incised or divided. In some embodiments, at least one layer comprises multiple cuts, incisions, or divisions through the layer such that at least one layer of the composite comprises several, separate pieces. FIG. 5 is a side view illustrating an exemplary composite backing comprising separate pieces for a first or top layer. In this aspect, the composite backing 26 comprises a first layer 28, a second adhesive layer 30, and a third layer 32. Any combination or all of the layers of the composite backing may be at least partially cut, incised or divided. In embodiments, at least one of the first layer or the third layer is at least partially cut, incised or divided.

Figure 4A:
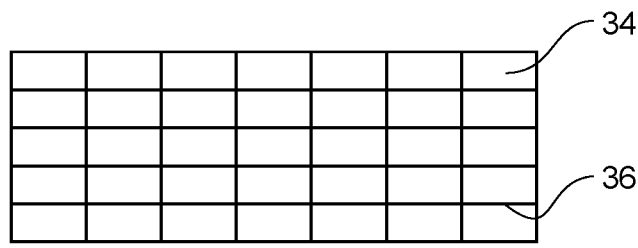
FIG. 4A is a top view illustration of a backing laminate layer.
Figure 4B:
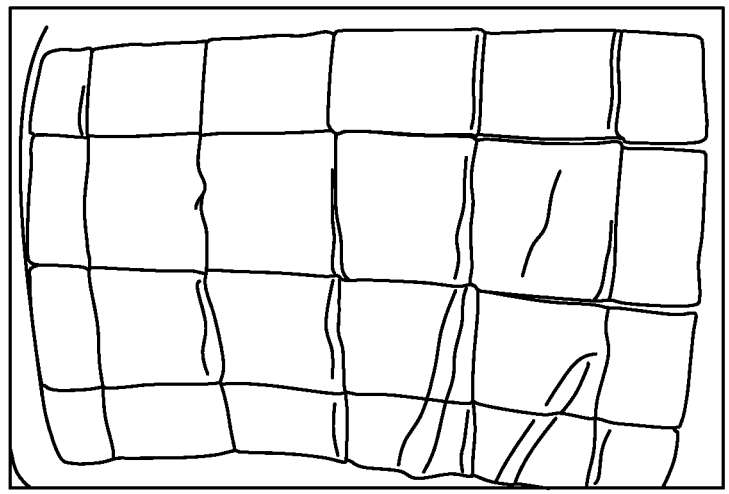
FIG. 4B is a top view image of a divided backing layer.

As seen FIG. 4A, one or more of layers of the composite backing is at least partially cut, incised or divided. In some embodiments, at least the third layer 32 is at least partially cut, incised or divided. In the embodiment as shown in FIGS. 4A-4B, the third layer is at least partially cut, incised or divided such that the third layer is comprised of a plurality of portions or pieces. These cuts may be formed partially or completely through the layer. In an embodiment, the layer is kiss cut such that at least one layer is cut while at least one of the layers (e.g. an elastic, flexible or stretchable layer) remains at least partially intact. In embodiments, the elastic or flexible polymer layer holds the layer comprising the cuts or incisions. In some embodiments, both the elastic, flexible or stretchable layer and the adhesive layers are at least partially intact. FIG. 4A shows an exemplary grid pattern for the cuts or incisions 36. In some embodiments, the cut layer is comprised of individually separated pieces of material 34 formed by the cuts in the layer material. The separate pieces may be any appropriate shape or form. In embodiments, the separated pieces are rectangular or square. It will be appreciated that the cuts may be regular or irregular in shape. In some embodiments, one or more of the pieces are connected at one or more connection regions. It will further be appreciated that the resulting pieces may be the same or different shapes. FIG. 4B shows a layer formed of individual rectangular pieces of material. In some embodiments, the cut layer is formed of multiple pieces of a relatively stiff material as described above. Motion of the relatively stiff layer within the composite and/or against the skin will be dissipated at the cuts. The layer comprising the cuts/pieces will behave like multiple patches of smaller area applied. Where the cut layer is formed of separate pieces, the layer is conformable and/or stretchable along with the movement of skin. Further, the adhesion of each piece helps an adjacent piece because they are held or adhered together similar to a continuous layer.

In some embodiments, each piece of the cut layer has a surface area of between about 5-50 $cm^2$. In some embodiments, each piece of the cut layer has a surface area of between about 10-30 $cm^2$. In some embodiments, each piece has a surface area of about 5 $cm^2$, 10 $cm^2$, 15 $cm^2$, 20 $cm^2$, 25 $cm^2$, 30 $cm^2$, 35 $cm^2$, 40 $cm^2$, 45 $cm^2$, or 50 $cm^2$. In some embodiments, the pieces of the layer may comprise a similar size. In other embodiments, the pieces of the layer comprise different sizes.

Figure 6:
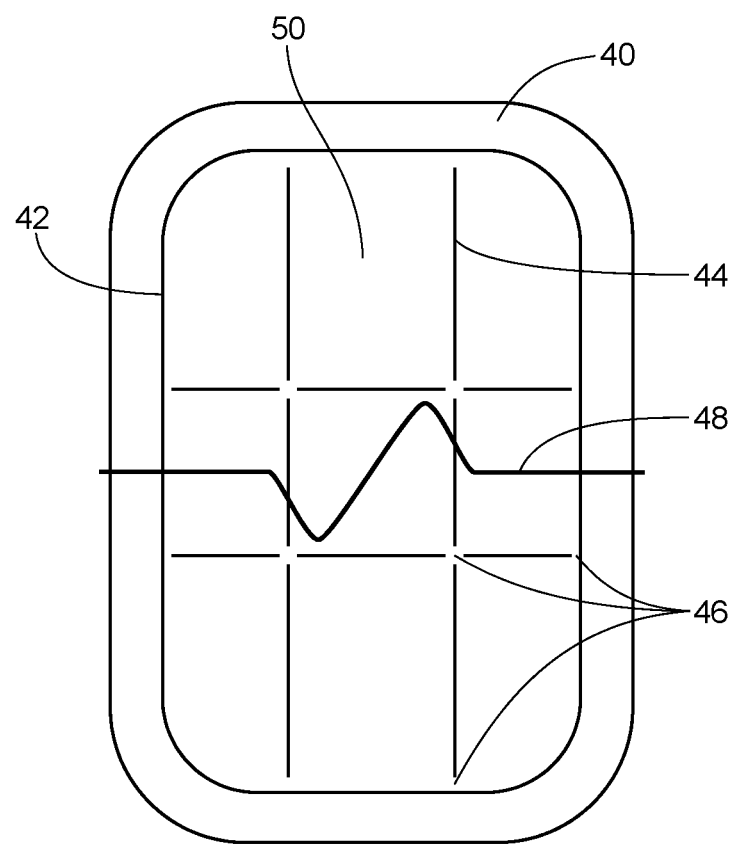
FIG. 6 is an illustration of a bottom-up view of a segmented patch layer in accord with embodiments described herein.

In some embodiments, the cuts, incisions or divisions extend at least partially along a planar surface of at least one layer of the composite backing. FIG. 6 is a top down view of a device as described herein in some embodiments. As seen in this embodiment, the cuts, incisions or divisions 4 extend along a portion of one or more layers 42 of the device, but do not extend across or along the entirety of the layer. In this embodiment, the cuts, incisions or divisions do not intersect. Instead, the layer(s) are intact at one or more of the edges and/or the areas where cross-wise cuts, incisions or divisions would intersect 46. Rather than being separate pieces, the partially cut portions of the layer 50 are at least partially connected. This embodiment, further shows the overhang of the first layer 40.

Example 2 describes preparation of an exemplary layer comprising a discretely cut layer. A flexible polymer material is applied to a carrier formed of paper or other inert material. The carrier serves as a substrate to form the discretely cut layer. In embodiments, the flexible polymer is as described above including, but not limited to, a thin (0.5-1.0 mil) polyurethane film. An occlusive material is applied to the flexible polymer material using a suitable adhesive as known in the art. In some embodiments, the adhesive is selected from a polyisobutylene (PIB), an acrylate, or a silicone adhesive or binding agent. The resulting laminate comprises the carrier, flexible polymer, adhesive, and occlusive material. The laminate is at least partially cut such that the occlusive layer is separated into separated pieces. At least a portion of the flexible polymer layer remains intact.

Example 3 describes preparation of a transdermal delivery system using a composite backing layer comprising an occlusive layer kiss-cut into rectangular pieces.

The device includes at least one adhesive/drug layer 14 adjacent the composite backing layer 12. In embodiments, the adhesive layer is an adhesive matrix comprising the active agent as described above. The adhesive layer adheres to the backing layer and/or skin at the administration site. Preferably, the adhesive layer 14 is positioned adjacent the third or bottom layer 22 of the composite backing 12. The adhesive layer matrix serves to release the active agent to the skin as well as secure the patch to the skin.

In an embodiment, the adhesive/drug layer is an adhesive hydrogel-containing composition as described in U.S. Pat. No. 8,728,445, which is incorporated herein by reference. One suitable hydrogel-containing composition is comprised of a single, continuous hydrophilic phase. Another suitable composition comprises a discontinuous hydrophobic phase and a hydrophilic phase that is either continuous or discontinuous. In an embodiment, the hydrogel composition comprises a discontinuous hydrophobic phase comprising at least one hydrophobic polymer, a plasticizer such as an elastomer, a tackifying resin and/or other excipients; and a hydrophilic phase comprised of at least one crosslinked hydrophilic polymer.

The hydrophobic polymer may be a hydrophobic pressure-sensitive adhesive (PSA) polymer. In some embodiments, the hydrophobic polymer is a thermosetting polymer. In embodiments, the hydrophobic PSA polymers are crosslinked butyl rubbers, wherein a "butyl rubber," as well known in the art, is an isoprene-isobutylene copolymer typically having an isoprene content in the range of about 0.5 to 3 wt %, or a vulcanized or modified version thereof, e.g., a halogenated (brominated or chlorinated) butyl rubber. In some embodiments, the hydrophobic PSA polymer is butyl rubber crosslinked with polyisobutylene. Other suitable hydrophobic polymers include, for example, natural rubber adhesives, vinyl ether polymers, polysiloxanes, polyisoprene, butadiene acrylonitrile rubber, polychloroprene, atactic polypropylene, and ethylene-propylene-diene terpolymers (also known as "EPDM" or "EPDM rubber") (available as Trilene® 65 and Trilene® 67 from Uniroyal Chemical Co., Middlebury, Conn.). Still other suitable hydrophobic PSAs will be known to those of ordinary skill in the art and/or are described in the pertinent texts and literature. See, for example, the Handbook of Pressure-Sensitive Adhesive Technology, 2nd Ed., Satas, Ed. (New York: Von Nostrand Reinhold, 1989). In some particular embodiments, the hydrophobic polymers are the crosslinked butyl rubbers available in the Kalar® series from Elementis Specialties, Inc. (Hightstown, N.J.), including Kalar® 5200, Kalar® 5215, Kalar® 5246, and Kalar® 5275.

In some embodiments, the hydrophobic phase comprises a plasticizer. By "plasticizer" is meant that the component tends to decrease the glass transition temperature of the hydrophobic polymer and/or reduce its melt viscosity. Suitable plasticizing elastomers are natural and synthetic elastomeric polymers, including, for example, AB, ABA, and "multiarmed" (AB)x block copolymers, where for example, A is a polymerized segment or "block" comprising aryl-substituted vinyl monomers, preferably styrene, α-methyl styrene, vinyl toluene, and the like, B is an elastomeric, conjugated polybutadiene or polyisoprene block, and x has a value of 3 or more. In some embodiments, the plasticizer is an elastomer including butadiene-based and isoprene-based polymers, particularly styrene-butadiene-styrene (SBS), styrene-butadiene (SB), styrene-isoprene-styrene (SIS), and styrene-isoprene (SI) block copolymers, where "S" denotes a polymerized segment or "block" of styrene monomers, "B" denotes a polymerized segment or block of butadiene monomers, and "I" denotes a polymerized segment or block of isoprene monomers. Other suitable elastomers include radial block copolymers having a SEBS backbone (where "E" and "B" are, respectively, polymerized blocks of ethylene and butylene) and I and/or SI arms. Natural rubber (polyisoprene) and synthetic polyisoprene can also be used.

In some embodiments, the hydrophobic phase comprises a tackifying resin. The tackifying resin may be a relatively low molecular weight resin (weight average molecular weight generally less than about 50,000) having a fairly high glass transition temperature. Tackifying resins include, for example, rosin derivatives, terpene resins, and synthetic or naturally derived petroleum resins. In some embodiments, the tackifying resin is selected from the group of non-polar tackifying resins, such as Regalrez® 1085 (a hydrogenated hydrocarbon resin) and Regalite® Resins such as Regalite® 1900, available from Hercules, Escorez 1304 (also a hydrocarbon resins) and Escorez® 1102 available from Exxon Chemical Company, Wingtack® 95 (a synthetic polyterpene resin), or Wingtack® 85, available from Goodyear Tire and Rubber.

In some embodiments, the hydrophobic phase comprises an optional antioxidant which serves to enhance the oxidative stability of the hydrogel composition. Other suitable plasticizers, tackifiers, and antioxidants are known in the art such as those described in U.S. Pat. No. 8,728,445, which is incorporated herein by reference.

In some embodiments, the composition comprises a discontinuous hydrophilic phase comprised of at least one crosslinked hydrophilic polymer that is insoluble in water under standard conditions of storage and use, but is water-swellable. In embodiments, the degree of crosslinking is selected so that the polymer will not melt during manufacture of the composition. Suitable hydrophilic polymers include, but are not limited to: crosslinked cellulosic polymers (such as crosslinked sodium carboxymethylcellulose); crosslinked acrylate polymers and copolymers; carbomers, i.e., hydroxylated vinylic polymers also referred to as "interpolymers," which are prepared by crosslinking a monoolefinic acrylic acid monomer with a polyalkyl ether of sucrose (commercially available under the trademark Carbopol® from the B. F. Goodrich Chemical Company); crosslinked acrylamide-sodium acrylate copolymers; gelatin; vegetable polysaccharides, such as alginates, pectins, carrageenans, or xanthan; starch and starch derivatives; and galactomannan and galactomannan derivatives. One particular crosslinked hydrophilic polymer is crosslinked sodium CMC, available as Aquasorb® A500 from Aqualon, a division of Hercules, Inc.

In some embodiments, the composition comprises a continuous hydrophilic phase. The continuous hydrophilic phase comprises a water-swellable, water-insoluble polymer, a blend of a hydro hydrophilic polymer and a complementary oligomer capable of hydrogen bonding thereto, and an optional low molecular weight plasticizer.

The water-swellable, water-insoluble polymer is generally capable of at least some degree of swelling when immersed in an aqueous liquid but is insoluble in water within a selected pH range, generally up to a pH of at least about 7.5 to 8.5. The polymer may be comprised of a cellulose ester, for example, cellulose acetate, cellulose acetate propionate (CAP), cellulose acetate butyrate (CAB), cellulose propionate (CP), cellulose butyrate (CB), cellulose propionate butyrate (CPB), cellulose diacetate (CDA), cellulose triacetate (CTA), or the like. These cellulose esters are described in U.S. Pat. Nos. 1,698,049, 1,683,347, 1,880,808, 1,880,560, 1,984,147, 2,129,052, and 3,617,201, and may be prepared using techniques known in the art or obtained commercially. Commercially available cellulose esters suitable herein include CA 320, CA 398, CAB 381, CAB 551, CAB 553, CAP 482, CAP 504, all available from Eastman Chemical Company, Kingsport, Tenn. Such cellulose esters typically have a number average molecular weight of between about 10,000 and about 75,000. Other suitable water-swellable polymers are known in the art as described, for example, in U.S. Pat. No. 8,728,445, incorporated by reference herein.

The hydrogel composition may also include conventional additives such as fillers, preservatives, pH regulators, softeners, thickeners, pigments, dyes, refractive particles, stabilizers, toughening agents, detackifiers, pharmaceutical agents, and permeation enhancers. In those embodiments wherein adhesion is to be reduced or eliminated, conventional detackifying agents may also be used. These additives, and amounts thereof, are selected in such a way that they do not significantly interfere with the desired chemical and physical properties of the hydrogel composition.

Absorbent fillers may be advantageously incorporated to control the degree of hydration when the adhesive is on the skin or other body surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, woven and non-woven paper and cotton materials. Other suitable fillers are inert, i.e., substantially non-adsorbent, and include, for example, polyethylenes, polypropylenes, polyurethane polyether amide copolymers, polyesters and polyester copolymers, nylon and rayon. A preferred filler is colloidal silica, e.g., Cab-O-Sil® (Cabot Corporation, Boston Mass.).

Preservatives include, by way of example, p-chloro-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

Compounds useful as pH regulators include, but are not limited to, glycerol buffers, citrate buffers, borate buffers, phosphate buffers, or citric acid-phosphate buffers may also be included so as to ensure that the pH of the hydrogel composition is compatible with that of an individual's body surface.

Suitable softeners include citric acid esters, such as triethylcitrate or acetyl triethylcitrate, tartaric acid esters such as dibutyltartrate, glycerol esters such as glycerol diacetate and glycerol triacetate; phthalic acid esters, such as dibutyl phthalate and diethyl phthalate; and/or hydrophilic surfactants, preferably hydrophilic non-ionic surfactants, such as, for example, partial fatty acid esters of sugars, polyethylene glycol fatty acid esters, polyethylene glycol fatty alcohol ethers, and polyethylene glycol sorbitan-fatty acid esters.

Preferred thickeners herein are naturally occurring compounds or derivatives thereof, and include, by way of example: collagen; galactomannans; starches; starch derivatives and hydrolysates; cellulose derivatives such as methyl cellulose, hydroxypropylcellulose, hydroxyethyl cellulose, and hydroxypropyl methyl cellulose; colloidal silicic acids; and sugars such as lactose, saccharose, fructose and glucose. Synthetic thickeners such as polyvinyl alcohol, vinylpyrrolidone-vinylacetate-copolymers, polyethylene glycols, and polypropylene glycols may also be used.

In embodiments, the adhesive drug layer is a composition that phase separates when moist as described in U.S. Pat. No. 8,481,059, which is incorporated herein by reference.

The adhesive/drug layer comprises one or more drugs, active agents, and/or therapeutic agents. One or more active agents can be included in the composition of the invention. Suitable active agents that may be incorporated into the adhesives of the invention, include the broad classes of compounds normally delivered through body surfaces and membranes such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; anti-inflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vesicants; and combinations thereof.

In some embodiments, the adhesive/drug layer comprises one or more drugs, active agents, and/or therapeutic agents for the treatment of Alzheimer's disease, dementia, and schizophrenia. In some embodiments, adhesive/drug layer comprises one or more drugs including, but not limited to donepezil and/or memantine.

The adhesive/drug layer may further comprise one or more permeation enhancers. With some active agents, it may be desirable to administer the agent along with a suitable permeation enhancer in order to achieve a therapeutically effective flux through the skin or mucosa. Selection of suitable permeation enhancers will depend upon the agent being delivered, as well as the enhancer's compatibility with the other components of the adhesive. Exemplary permeation enhancers include, by way of illustration and not limitation, sulfoxides such as dimethylsulfoxide and decylmethylsulfoxide; ethers such as diethylene glycol monoethyl ether and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; the 1-substituted azacycloheptan-2-ones, particularly 1-n-dodecylcyclazacycloheptan-2-one; alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid; and mixtures thereof.

The release of active agents "loaded" into the adhesive of the invention typically involves both absorption of water and desorption of the agent via a swelling-controlled diffusion mechanism. Active agent-containing adhesives may be included in adhesive cushions, wound dressings, transdermal drug delivery devices and the like.

In embodiments, the transdermal delivery system includes an optional release liner 16 that at least partially contacts the adhesive layer. The release liner is a removable covering that prevents loss of the active agent from the adhesive layer during storage and/or protects the device against contamination. The release liner is typically a disposable layer that is removed prior to application of the device to the treatment site. In some embodiments, the release liner preferably does not absorb components of the adhesive layer, including the active agent. In some embodiments, the release liner preferably impermeable to components of the adhesive layer (including the active agent) and prevents release of components of the adhesive layer through the release liner. By impermeable, it is meant that the release liner prevents all or substantially all of the components of the adhesive layer from passing completely through the release liner. In some embodiments, the release liner is easily removed or stripped from the adhesive/drug layer without removing a portion or a substantial portion of the adhesive drug layer. In some embodiments, the release liner is formed of one or more of a film, non-woven fabric, woven fabric, laminate, and combinations thereof. In some embodiments, the release liner is a silicone-coated polymer film or paper. In some non-limiting embodiments, the release liner is a silicone-coated polyethylene terephthalate (PET) film, a polyester film, a silicone-coated polyester film, a fluorocarbon film, or a fluorocarbon or fluorosilicone coated polymer film. In some embodiments, the material for the release liner is treated with one or more of silicone, fluorocarbons or fluorosilicones. In one embodiment, the release liner is comprised of fluorocarbon or fluorosilicone coated PET film. In other embodiments, the release liner is comprised of a polyester foil or other metalized laminate. In some embodiments, the release liner may include features to increase ease of removal. In some embodiment, the release liner includes a slit or cut 48 as shown in FIG. 6 to assist in removal of the liner from the device.

The activity of a transdermal delivery system is defined (and dependent upon) the release rate of the active agent from the system, the total duration of release from the system, and the surface area of the delivery system.

III. Methods of Treatment

Based on the exemplary compositions and devices described herein, and the data showing release effective long term administration of the device, a method for prolonged or long term administration of an active agent is provided herein.

The methods and systems described herein may be used for treating or preventing any condition receptive to treatment with a therapeutic agent, drug or active agent as described herein. The methods and systems described herein are particularly useful for long term transdermal administration of the therapeutic agent, drug or active agent. In embodiments, the transdermal device is suitable for administration of the active agent or agents for at least about 3-14 days or more.

IV. Examples

The following examples are illustrative in nature and are in no way intended to be limiting.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, patent publications, and other publications mentioned herein are hereby incorporated by reference in their entirety. Where a patent, application, or publication contains express definitions, those definitions should be understood to apply to the incorporated patent, application or publication in which they are found and not to the present application unless otherwise indicated.

Example 1

Manufacture of Transdermal Delivery System with Composite Backing

A thin layer of a stretchable or flexible polymer (1-40 mil) is laminated onto an occlusive backing (e.g. Scotchpack™ 1012, polyester film laminate) with an adhesive such as polyisobutylene (PIB), acrylate, a silicone adhesive or other binding agent to form a laminate consisting of occlusive backing/adhesive/stretchable or flexible polymer.

An adhesive drug formulation is blended, coated on a release liner, and dried. The adhesive drug formulation is laminated on the stretchable or flexible polymer side of the backing laminate.

Example 2

Manufacture of Backing Laminate

A thin polyurethane film (0.5 to 1.0 mil) with a paper carrier (e.g. 3M COTran™ 9701 Backing, 2 mil polyurethane film) is used as the top layer. An occlusive backing, (e.g. Scotchpack™ 1012, polyester film laminate) is laminated on the polyurethane film with an adhesive such as polyisobutylene (PIB), acrylate, a silicone adhesive or other binding agent to make a quad laminate consisting of a paper carrier/polyurethane/adhesive/occlusive backing.

The occlusive backing layer is kiss-cut to divide it into multiple, discrete pieces as attached on the flexible elastic layer such as a polyurethane film.

The size of each discrete occlusive backing piece ranges from about 10 cm² to about 40 cm² depending on requirements. Each of the discrete backing pieces are adhered or stuck together on the polyurethane film by the adhesive. The laminate may be rolled in further converting process.

Example 3

Manufacture of Transdermal Delivery System

An adhesive drug formulation is blended, coated on a release liner, and dried. The adhesive drug formulation is laminated on a discretely, kiss-cut occlusive film side of the backing laminate as prepared in Example 2. The paper carrier is removed from the polyurethane side to leave the final formulation laminate. It is die-cut into a required size which is a large patch containing multiple discrete pieces of occlusive film but all other layers are continuous. An exemplary patch is shown in FIG. 4B.

Example 4

Manufacture of Transdermal Delivery System with Composite Backing

A thin layer of KOB 053 woven polyester fabric (Karl Otto GmbH & Co.) is laminated onto a Scotchpak™ 1012 (3M®) polyester film laminate with Duro-Tak 87-2052, an acrylate copolymer pressure sensitive adhesive (Henkel Corporation) to form a laminate consisting of woven fabric/adhesive/polymer film.

An adhesive drug formulation is blended, coated on a release liner, and dried. The adhesive drug formulation is laminated on the polymer film side of the backing laminate.

Embodiments

1. A composite backing layer for use in a transdermal patch, comprising:
    a first layer comprised of a polymer fabric or a polymer film having a stretchability of at least about 5% in at least one direction;
    a second layer comprised of one or more adhesive polymers; and
    a third layer comprised of one or more polymers;
        wherein the first and second layers are in contact and the second and third layers are in contact.
2. The composite backing layer of embodiment 1, wherein the polymer fabric or polymer film is comprised of one or more polymers selected from polyesters, polyethylenes, polypropylenes, polyvinylchloride, polyethylene vinyl acetate or copolymers thereof, and polyurethanes.
3. The composite backing layer of the combined or separate embodiments 1-2, wherein the first layer is selected from a woven polymer fabric, a non-woven polymer fabric, a polymer laminate, and a polymer/metal laminate.
4. The composite backing layer of the combined or separate embodiments 1-3, wherein the first layer has a thickness of about 0.5-10 mil.
5. The composite backing layer of the combined or separate embodiments 1-4, wherein one or more of the polymers of the second layer polymers has at least one of (i) a tensile strength of less than about 10 MPa and (ii) an elongation of at least about 50%.
6. The composite backing layer of the combined or separate embodiments 1-5, wherein the one or more polymers of the second layer are selected from acrylates, acrylate copolymers, polyisobutylene, silicone, polystyrene butyl rubber, polyethylene vinyl acetate and copolymers thereof, and plasticized polymers.
7. The composite backing of the combined or separate embodiments 1-6, wherein one or more of the adhesive polymers of the second layer have a shear strength that is less or equal to about 1-25% of the tensile strength for the polymer.
8. The composite backing layer of the combined or separate embodiments 1-7, wherein the second layer has a thickness of about 0.5-30 mil.
9. The composite backing layer of the combined or separate embodiments 1-8, wherein the third layer has a thickness of about 1-40 mil.

10. The composite backing layer of the combined or separate embodiments 1-9, wherein the third layer is attached to an adhesive drug layer comprising one or more drugs.
11. The composite backing layer of the combined or separate embodiments 1-10, wherein the first layer, second layer, and third layer are laminated.
12. The composite backing layer of the combined or separate embodiments 1-11, wherein at least one of the first layer or the third layer is at least partially cut.
13. A transdermal patch for delivery of an active agent, comprising:
(a) a composite backing layer comprising:
a first layer comprised of a polymer fabric or a polymer film having a stretchability of at least about 5% in at least one direction;
a second layer comprised one or more adhesive polymers; and
a third layer comprised of one or more polymers;
wherein the first layer, second layer, and third layers are arranged in contact as a composite;
(b) an adhesive drug layer comprising the active agent; and
(c) a release liner.
14. The transdermal patch of embodiment 13, wherein the first layer polymer fabric or polymer film is comprised of one or more polymers selected from polyesters, polyethylenes, polypropylenes, polyvinylchloride, polyethylene vinyl acetate or copolymers thereof, and polyurethanes.
15. The transdermal patch of the combined or separate embodiments 13-14, wherein the first layer is selected from an occlusive polymer film, a polymer laminate, a polymer/metal laminate, a breathable polymer film, a woven polymer fabric and a non-woven polymer fabric.
16. The transdermal patch of the combined or separate embodiments 13-15, wherein the first layer has a thickness of about 0.5-10 mil.
17. The transdermal patch of the combined or separate embodiments 13-16, wherein the one or more polymers of the second layer are selected from acrylates, acrylate copolymers, polyisobutylene, silicone, polystyrene butyl rubber, polyethylene vinyl acetate and copolymers thereof, and plasticized polymers.
18. The transdermal patch of the combined or separate embodiments 13-17, wherein one or more of the adhesive polymers of the second layer have a shear strength that is less or equal to about 1-25% of the tensile strength for the polymer.
19. The transdermal patch of the combined or separate embodiments 13-18, wherein the second layer has a thickness of about 0.5-30 mil.
20. The transdermal patch of the combined or separate embodiments 13-19, wherein the third layer has a thickness of about 1-40 mil.
21. The transdermal patch of the combined or separate embodiments 13-20, wherein the release liner is formed of a material selected from a silicone coated polyethylene terephthalate, a fluorocarbon, a fluorocarbon coated polyethylene terephthalate, and a fluorosilicone coated polyethylene terephthalate.
22. A method of transdermally administering an active agent, comprising:
removing a release liner from the transdermal patch or a patch comprising a backing of the combined or separate embodiments 1-21; and adhering the transdermal patch to the skin of a patient for a period up to about 10 days to deliver the active agent to said patient.
23. A composite backing layer for use in a transdermal patch, comprising:
a first layer comprised of a polymer fabric or a polymer film;
a second layer comprised of one or more polymers having at least one of (i) a tensile strength of less than about 10 MPa and (ii) an elongation of at least about 50%;
a third layer comprised of one or more stretchable polymers having a stretchability of at least about 10%;
wherein the first and second layers are in contact and the second and third layers are in contact.
24. The composite backing layer of embodiment 23, wherein the polymer fabric or polymer film is comprised of one or more polymers selected from polyesters, polyethylenes, polypropylenes, polyvinylchloride, polyethylene vinyl acetate or copolymers thereof, and polyurethanes.
25. The composite backing layer of the combined or separate embodiments 23-24, wherein the first layer is selected from a woven, a non-woven polymer fabric, an occlusive polymer film, a polymer laminate, and a polymer/metal laminate.
26. The composite backing layer of the combined or separate embodiments 23-25, wherein the first layer has a thickness of about 0.5-10 mil.
27. The composite backing layer of the combined or separate embodiments 23-26, wherein the second layer is an adhesive layer.
28. The composite backing layer of embodiment 27, wherein adhesive layer is an adhesive tie layer.
29. The composite backing layer of the combined or separate embodiments 23-28, wherein the one or more polymers of the second layer are selected from acrylates, polyisobutylene, silicone, polystyrene butyl rubber, polyethylene vinyl acetate and copolymers thereof, and plasticized polymers.
30. The composite backing of the combined or separate embodiments 23-29, wherein the one or more polymers of the second layer have a low shear strength.
31. The composite backing layer of the combined or separate embodiments 23-30, wherein the second layer has a thickness of about 0.5-30 mil.
32. The composite backing layer of the combined or separate embodiments 23-31, wherein the third layer is a non-woven or woven fabric formed of one or more polymer fibers.
33. The composite backing layer of embodiment 32, wherein the one or more polymer fibers are formed of a polymer fiber selected from polyester, cotton, silk, polypropylene, nylon, polystyrene, polyvinylchloride, and polyurethanes.
34. The composite backing layer of the combined or separate embodiments 23-33, wherein the stretchable polymers have a stretchability of at least about 10% in at least one direction.
35. The composite backing layer of the combined or separate embodiments 23-34, wherein the third layer has a thickness of about 1-40 mil.
36. The composite backing layer of the combined or separate embodiments 23-35, wherein the third layer is attached to an adhesive drug layer comprising one or more drugs.

37. The composite backing layer of embodiment 36, wherein the backing layer is impermeable to the one or more drugs.
38. The composite backing layer of the combined or separate embodiments 23-37, wherein the backing layer is occlusive.
39. The composite backing layer of the combined or separate embodiments 23-38, wherein the first layer, second layer, and third layer are laminated.
40. The composite backing layer of the combined or separate embodiments 23-39, wherein the backing has a surface area of at least about 5-45 cm².
41 A transdermal patch for delivery of an active agent, comprising:
   (a) a composite backing layer comprising:
      a first layer comprised of a polymer fabric or a polymer film;
      a second layer comprised of one or more polymers having at least one of (i) a tensile strength of less than about 10 MPa and (ii) an elongation of at least about 50%;
      a third layer comprised of a material selected from one or more stretchable polymers having a stretchability of at least about 10%, a woven fabric and a non-woven fabric;
      wherein the first layer, second layer, and third layers are arranged in contact as a composite;
   (b) an adhesive drug layer comprising the active agent; and
   (c) a release liner.
42. The transdermal patch of embodiment 41, wherein the first layer polymer fabric or polymer film is comprised of one or more polymers selected from polyesters, polyethylenes, polypropylenes, polyvinylchloride, polyethylene vinyl acetate or copolymers thereof, and polyurethanes.
43. The transdermal patch of embodiment 41, wherein the first layer is selected from an occlusive polymer film, a polymer laminate, a polymer/metal laminate, a breathable polymer film, a woven polymer fabric and a non-woven polymer fabric.
44. The transdermal patch of the combined or separate embodiments 41-43, wherein the first layer has a thickness of about 0.5-10 mil.
45. The transdermal patch of the combined or separate embodiments 41-44, wherein the second layer is an adhesive layer.
46. The transdermal patch of embodiment 45, wherein the adhesive layer is an adhesive tie layer.
47. The transdermal patch of the combined or separate embodiments 41-46, wherein the one or more polymers of the second layer are selected from acrylates, polyisobutylene, silicone, polystyrene butyl rubber, polyethylene vinyl acetate and copolymers thereof, and plasticized polymers.
48. The transdermal patch of the combined or separate embodiments 41-47, wherein the one or more polymers of the second layer have a low shear strength.
49. The transdermal patch of the combined or separate embodiments 41-48, wherein the second layer has a thickness of about 0.5-30 mil.
50. The transdermal patch of the combined or separate embodiments 41-49, wherein the third layer is a non-woven or woven fabric formed of one or more polymer fibers.
51. The transdermal patch of embodiment 50, wherein the one or more polymer fibers are formed of a polymer fiber selected from polyester, cotton, silk, polypropylene, nylon, polystyrene, polyvinylchloride, and polyurethanes.
52. The transdermal patch of the combined or separate embodiments 41-51, wherein the stretchable polymers have a stretchability of at least about 10% in at least one direction.
53. The transdermal patch of the combined or separate embodiments 41-52, wherein the third layer has a thickness of about 1-40 mil.
54. The transdermal patch of the combined or separate embodiments 41-53, wherein the backing layer is occlusive.
55. The transdermal patch of the combined or separate embodiments 41-54, wherein the backing layer is impermeable to the active agent.
56. The transdermal patch of the combined or separate embodiments 41-55, wherein the adhesive drug layer is comprised of an adhesive matrix.
57. The transdermal patch of the combined or separate embodiments 41-56, wherein the release liner is a silicone coated material.
58. The transdermal patch of embodiment 57, wherein the release liner is a silicone coated PET, fluorocarbon, or fluorocarbon coated PET.
59. The transdermal patch of the combined or separate embodiments 41-58, wherein the patch has a surface area of at least about 5-45 cm².
60. A transdermal patch for delivery of an active agent, comprising:
   (a) a backing layer;
   (b) an adhesive drug layer comprising the active agent;
   (c) a stretchable layer having a stretchability of at least about 10%, wherein the stretchable layer is embedded within the adhesive drug layer; and
   (d) a release liner.
61. The patch of embodiment 60, wherein the stretchable layer is comprised of at least one polymer having a stretchability of at least about 10%, a woven polymer fiber fabric, and a non-woven polymer fiber fabric.
62. A composite backing layer for use in a transdermal patch, comprising:
   a first elastic or flexible layer comprised of one or more polymers having at least one of (i) a tensile strength of less than about 10 MPa or (ii) an elongation of at least about 50%;
   a second adhesive layer; and
   a third layer comprised of a plurality of separated pieces of an occlusive or substantially occlusive material.
63. The composite backing of embodiment 62, wherein the first layer is formed of a woven or non-woven polymer fabric or an elastic polymer film.
64. The composite backing of the combined or separate embodiments 62-63, wherein the elastic polymer film is selected from a polyurethane film, a thermoplastic polyester elastomer film, and a polyethylene vinyl acetate film.
65. The composite backing of the combined or separate embodiments 62-64, wherein the first layer has a thickness of about 0.5-5 mil.
66. The composite backing of the combined or separate embodiments 62-65, wherein the second adhesive layer is comprised of one or more adhesives.
67. The composite backing of embodiment 66, wherein the adhesive is selected from an acrylic adhesive, a polyisobutylene adhesive, and a silicone adhesive.

68. The composite backing of the combined or separate embodiments 62-67, wherein the second adhesive layer has a thickness of about 0.5-2 mil.
69. The composite backing of the combined or separate embodiments 62-68, wherein the occlusive or substantially occlusive material is selected from polyesters, polyethylenes, a polyethylene vinylacetate, polypropylenes, polystyrenes, polyvinylchloride or copolymers thereof, and nylon.
70. The composite backing of embodiment 69, wherein the third layer is a laminate.
71. The composite backing of the combined or separate embodiments 62-70, wherein the separated pieces are square or rectangular.
72. The composite backing of the combined or separate embodiments 62-71, wherein the third layer has a thickness of about 1-5 mil.
73. A method of transdermally administering an active agent, comprising:
    removing a release liner from the transdermal patch or a patch comprising a backing of the combined or separate embodiments 1-72; and
    adhering the transdermal patch to the skin of a patient for a period up to about 10 days to deliver the active agent to said patient.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, patent publications, and other publications mentioned herein are hereby incorporated by reference in their entirety. Where a patent, application, or publication contains express definitions, those definitions should be understood to apply to the incorporated patent, application or publication in which they are found and not to the present application unless otherwise indicated.

It is claimed:

1. A method for treating Alzheimer's disease in a subject, comprising:
    applying a transdermal patch to skin of the subject, wherein the transdermal patch is comprised of a composite backing layer comprised of
    (i) a first layer comprised of a polymer fabric or a polymer film comprised of one or more polymers selected from polyesters, and polyethylenes;
    (ii) a second layer comprised of one or more adhesive polymers, the one or more adhesive polymers being acrylate copolymers; and
    (iii) a third layer comprised of a polyethylene terephthalate/ethylene-vinyl acetate laminate;
    wherein the first and second layers are in contact and the second and third layers are in contact, and
    wherein the third layer comprises cuts formed at least partially through the third layer; and
    an adhesive matrix drug layer laminated to the third layer, the adhesive matrix drug layer comprising donepezil.

2. The method of claim 1, wherein the first layer has a thickness of about 10-25 mil.

3. The method of claim 1, wherein one or more of the adhesive polymers of the second layer has at least one of (i) a tensile strength of less than 10 MPa and (ii) an elongation of at least 50%.

4. The method of claim 1, wherein the second layer has a thickness of about 0.5-30 mil.

5. The method of claim 1, wherein the third layer has a thickness of about 1-40 mil.

6. The method of claim 1, wherein the first layer, second layer, and third layer are laminated.

7. A method for delivery of donepezil through skin, comprising:
    applying a transdermal patch to the skin of a subject, wherein the transdermal patch is comprised of a composite backing layer comprising
    (i) a first layer comprised of a polymer fabric or a polymer film comprised of one or more polymers selected from polyesters, and polyethylenes;
    (ii) a second layer comprised of one or more adhesive polymers, the one or more adhesive polymers being acrylate copolymers; and
    (iii) a third layer comprised of a polyethylene terephthalate/ethylene-vinyl acetate laminate,
    wherein the third layer comprises cuts formed at least partially through the third layer;
    wherein the first layer, second layer, and third layers are arranged in contact as a composite;
    (iv) an adhesive drug layer comprising donepezil, the adhesive drug layer laminated to the third layer; and
    (v) a release liner;
    wherein donepezil is delivered through the skin upon removal of the release liner.

8. The method of claim 7, wherein the first layer has a thickness of about 10-25 mil.

9. The method of claim 7, wherein the second layer has a thickness of about 0.5-30 mil.

10. The method of claim 7, wherein the third layer has a thickness of about 1-40 mil.

11. The method of claim 7, wherein the release liner is formed of a material selected from a silicone coated polyethylene terephthalate, a fluorocarbon, a fluorocarbon coated polyethylene terephthalate, and a fluorosilicone coated polyethylene terephthalate.

\* \* \* \* \*